US006989441B2

(12) United States Patent
Curtis

(10) Patent No.: US 6,989,441 B2
(45) Date of Patent: Jan. 24, 2006

(54) 25466, A HUMAN TRANSPORTER FAMILY MEMBER AND USES THEREFOR

(75) Inventor: Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 193 days.

(21) Appl. No.: 10/074,547

(22) Filed: Feb. 12, 2002

(65) Prior Publication Data

US 2002/0132301 A1 Sep. 19, 2002

Related U.S. Application Data

(60) Provisional application No. 60/269,072, filed on Feb. 15, 2001.

(51) Int. Cl.
*C07H 21/02* (2006.01)
*C07H 21/04* (2006.01)
*C12P 21/06* (2006.01)
*C12N 15/00* (2006.01)
*C12N 5/00* (2006.01)

(52) U.S. Cl. ............... 536/23.1; 435/69.1; 435/320; 435/325; 530/350

(58) Field of Classification Search ............... 536/23.1; 435/320.1, 325, 69.1; 530/350
See application file for complete search history.

(56) References Cited

U.S. PATENT DOCUMENTS

2003/0219745 A1 * 11/2003 Tang et al. .............. 435/6
2004/0024183 A1 * 2/2004 Lee et al. ............... 530/350

FOREIGN PATENT DOCUMENTS

WO    WO 01/60860 A2 *  8/2001
WO    WO 02/40715 A2    5/2002

OTHER PUBLICATIONS

Bover et al. (1998), Cell. Mol. Biol. 44(3): 493–504.*
Price et al. (1998), Cloning and sequencing of four new mammalian monocarboxylate transporter (MCT) homologues confirms the existence of a transporter family with an ancient past, Biochem J. 329: 321–328.*
Zhao et al. (2001), Expression and Distribution of Lactate/Monocarboxylate Transporter Isoforms in Pancreatic Islets and the Exocrine Pancreas, Diabetes 50: 361–366.*
Galic et al. (2003), The loop between helix 4 and helix 5 in the monocarboxylate transporter MCT1 is important for substrate selection and protein stability, Biochem. J. 376: 413–422.*
Enerson et al. (2003), Molecular Features, Regulation, and Function of Monocarboxylate Transporters: Implications for Drug Delivery, J. Pharm. Sci. 92(8): 1531–1544.*

Juel et al. (1999), Lactate transport in skeletal muscle—role and regulation of the monocarboxylate transporter, J. Physiol. 517(3): 633–642.*

Havelaar, Adrie C. et al. "Purification of the Lysosomal Sialic Acid Transporter", *The Journal of Biological Chemistry*, vol. 273, No. 51, Dec. 18, 1988, pp. 34568–34574.

Price, N.T., et al. "MOT5_HUMAN," May 2000 (sequence) Swiss–Prot: [online] Geneva, Switzerland: Swiss Institute of Bioinformatics [retrieved on Aug. 17, 2002]. Retrieved from the Internet: <URL: http://www.expasy.ch/sprot/>. Accession No.: O15374.

"Mus Musculus 18 days embryo whole body cDNA" Feb. 8, 2002, (sequence) EMBL [online], Hinxton, Cambrdige, UK: European Bioinformatics Institute [retrieved on Jul. 10, 2002]. Retrieved from the Internet: <URL: http://srs6.ebi.ac.uk/srs6bin/cgi–bin/wget/>. EMBL Accession No. AK003423.

"*Homo Sapiens* cDNA FLJ30794 fis, clone FEBRA20001093, weakly similar to monocarboxylate transporter 4" Oct. 31, 2001 (sequence) EMBL [online], Hinxton, Cambrdige, UK: European Bioinformatics Institute [retrieved on Jul. 10, 2002]. Retrieved from the Internet: <URL: http://srs6.ebi.ac.uk/srs6bin/cgi–bin/wget/>. EMBL Accession No. AK055356.

Halestrap, Andrew P. et al. "The Proton–Linked Monocarboxylate Transporter (MCT) family: Structure, Function and Regulation." *Biochemical Journal*, vol. 343, No. 2 (Oct. 15, 1999), pp. 281–299.

Takanaga, Hitomi et al., "cDNA Cloning and Functional Characterization of rat Intestinal Monocarboxylate Transporter", *Biochemical and Biophysical Research Communications*, vol. 217, No. 1 (Dec. 5, 1995), pp. 370–377.

(Continued)

Primary Examiner—Janet Andres
(74) Attorney, Agent, or Firm—Millennium Pharmaceuticals, Inc.

(57) ABSTRACT

The invention provides isolated nucleic acids molecules, designated 25466 nucleic acid molecules, which encode novel transporter molecules. The 25466 transporter molecules are homologous to monocarboxylate (MCT) transporters, and in particular to SLC16 family members. The invention also provides antisense nucleic acid molecules, recombinant expression vectors containing 25466 nucleic acid molecules, host cells into which the expression vectors have been introduced, and nonhuman transgenic animals in which a 25466 gene has been introduced or disrupted. The invention still further provides isolated 25466 proteins, fusion proteins, antigenic peptides and anti-25466 antibodies. Diagnostic and therapeutic methods utilizing compositions of the invention are also provided.

11 Claims, 1 Drawing Sheet

OTHER PUBLICATIONS

Jackson, Vicky N. et al., "Cloning of the Monocarboxylate Transporter Isoform MCT2 From Rat Testis Provides Evidence that Expression in Tissues is Species–Specific and May Involve Post–Transcriptional Regulation." *Biochemical Journal*, vol. 324, No. 2, (1997), pp. 447–453.

Garcia, Christine Kim et al., "cDNA Cloning of the Human Monocarboxylate Transporter 1 and Chromosomal Localization of the SLC16A1 Locus to 1p13.2–2–p12", *Genomics*, vol. 23, No. 2, (Sep. 15, 1994), pp. 500–503.

Kim, Do Kyung, et al, "Expression Cloning of a Na+–Independent Aromatic Amino Acid H+/Monocarboxylate transporters", *Journal of Biological Chemistry*, vol. 276, No. 20 (May 18, 2001), pp. 17221–17228.

WIPF, D., et al, "Conservation of Amino Acid Transporters in Fungi, Plants and Animals" *Trends in Biochemical Sciences*, vol. 27, No. 3 (Mar. 1, 2002), pp. 139–147.

* cited by examiner

SEQUENCE LISTING

<160> NUMBER OF SEQ ID NOS: 8

<210> SEQ ID NO 1
<211> LENGTH: 4419
<212> TYPE: DNA
<213> ORGANISM: homo sapiens
<220> FEATURE:
<221> NAME/KEY: CDS
<222> LOCATION: (449)...(1981)

<400> SEQUENCE: 1

```
gtcgacccac gcgtccgcaa gagtgtgcat gtgaggtgac tgcatttttt ttccctgcca      60
aaccagaatt agccggtata ggaatgaacg agcatgaaga tttgaaattg ctccgattgg     120
aaggaagccc aggttaggtt tgggcacctc caaacgcacc cgttttaaag ccacctggac     180
tgaggcgtcg agctttcagc tccaccaaac gctcacctgg cctggcagcg agcggcggaa     240
gagcccggga gcccctcaca gagcgcaccg agccgggcgg agagctgagc cgcaggcacc     300
cgcgtctcca ggatgatagg cgacattgca acaaatctct acacccagca gctcaggggg     360
ctccaagcag agcagcaagt tcgaggatcc gggcgtggag ccgagtgagg ccgcagccca     420
gcgggcctcg ggcgaaaaat cttggaaa atg tat acc agt cat gaa gat att      472
                                 Met Tyr Thr Ser His Glu Asp Ile
                                  1               5 ggg tat gat ttt gaa gat ggc ccc aaa gac aaa aag aca ctg aag ccc      520
Gly Tyr Asp Phe Glu Asp Gly Pro Lys Asp Lys Lys Thr Leu Lys Pro
         10                  15                  20 cac cca aac att gat ggc gga tgg gct tgg atg atg gtg ctc tcc tct      568
His Pro Asn Ile Asp Gly Gly Trp Ala Trp Met Met Val Leu Ser Ser
 25                  30                  35                  40 ttc ttt gtg cac atc ctc atc atg ggc tcc cag atg gcc ctg ggt gtc      616
Phe Phe Val His Ile Leu Ile Met Gly Ser Gln Met Ala Leu Gly Val
                 45                  50                  55 ctc aac gtg gaa tgg ctg gaa gaa ttc cac cag agc cgc ggc ctg acc      664
Leu Asn Val Glu Trp Leu Glu Glu Phe His Gln Ser Arg Gly Leu Thr
             60                  65                  70 gcc tgg gtc agc tcc ctc agc atg ggc atc acc ttg ata gtg ggc cct      712
Ala Trp Val Ser Ser Leu Ser Met Gly Ile Thr Leu Ile Val Gly Pro
         75                  80                  85 ttc atc ggc ttg ttc att aac acc tgt ggg tgc cgc cag act gcg atc      760
Phe Ile Gly Leu Phe Ile Asn Thr Cys Gly Cys Arg Gln Thr Ala Ile
     90                  95                 100 att gga ggg ctc gtc aac tcc ctg ggc tgg gtg ttg agt gcc tat gct      808
Ile Gly Gly Leu Val Asn Ser Leu Gly Trp Val Leu Ser Ala Tyr Ala
105                 110                 115                 120 gca aac gtg cat tat ctc ttc att act ttt gga gtc gca gct ggc ctg      856
Ala Asn Val His Tyr Leu Phe Ile Thr Phe Gly Val Ala Ala Gly Leu
                125                 130                 135 ggc agc ggg atg gcc tac ctg cca gcg gtg gtc atg gtg ggc agg tat      904
Gly Ser Gly Met Ala Tyr Leu Pro Ala Val Val Met Val Gly Arg Tyr
```

-continued

```
                 140                 145                 150
ttc cag aag aga cgc gcc ctc gcc cag ggc ctc agc acc acg ggg acc       952
Phe Gln Lys Arg Arg Ala Leu Ala Gln Gly Leu Ser Thr Thr Gly Thr
            155                 160                 165 gga ttc ggt acg ttc cta atg act gtg ctg ctg aag tac ctg tgc gca      1000
Gly Phe Gly Thr Phe Leu Met Thr Val Leu Leu Lys Tyr Leu Cys Ala
170                 175                 180 gag tac ggc tgg agg aat gcc atg ttg atc caa ggt gcc gtt tcc cta      1048
Glu Tyr Gly Trp Arg Asn Ala Met Leu Ile Gln Gly Ala Val Ser Leu
185                 190                 195                 200 aac ctg tgt gtt tgt ggg gcg ctc atg agg ccc ctc tct cct ggt aaa      1096
Asn Leu Cys Val Cys Gly Ala Leu Met Arg Pro Leu Ser Pro Gly Lys
                205                 210                 215 aac cca aac gac cca gga gag aaa gat gtg cgt ggc ctg cca gcg cac      1144
Asn Pro Asn Asp Pro Gly Glu Lys Asp Val Arg Gly Leu Pro Ala His
            220                 225                 230 tcc aca gaa tct gtg aag tca act gga cag cag gga aga aca gaa gag      1192
Ser Thr Glu Ser Val Lys Ser Thr Gly Gln Gln Gly Arg Thr Glu Glu
            235                 240                 245 aag gat ggt ggg ctc ggg aac gag gag acc ctc tgc gac ctg caa gcc      1240
Lys Asp Gly Gly Leu Gly Asn Glu Glu Thr Leu Cys Asp Leu Gln Ala
250                 255                 260 cag gag tgc ccc gat cag gcc ggg cac agg aag aac atg tgt gcc ctc      1288
Gln Glu Cys Pro Asp Gln Ala Gly His Arg Lys Asn Met Cys Ala Leu
265                 270                 275                 280 cgg att ctg aag act gtc agc tgg ctc acc atg aga gtc agg aag ggc      1336
Arg Ile Leu Lys Thr Val Ser Trp Leu Thr Met Arg Val Arg Lys Gly
                285                 290                 295 ttc gag gac tgg tat tcg ggc tac ttt ggg aca gcc tct cta ttt aca      1384
Phe Glu Asp Trp Tyr Ser Gly Tyr Phe Gly Thr Ala Ser Leu Phe Thr
            300                 305                 310 aat cga atg ttt gta gcc ttt att ttc tgg gct ttg ttt gca tac agc      1432
Asn Arg Met Phe Val Ala Phe Ile Phe Trp Ala Leu Phe Ala Tyr Ser
            315                 320                 325 agc ttt gtc atc ccc ttc att cac ctc cca gaa atc gtc aat ttg tat      1480
Ser Phe Val Ile Pro Phe Ile His Leu Pro Glu Ile Val Asn Leu Tyr
330                 335                 340 aac tta tcg gag caa aac gac gtt ttc cct ctg acg tca att ata gca      1528
Asn Leu Ser Glu Gln Asn Asp Val Phe Pro Leu Thr Ser Ile Ile Ala
345                 350                 355                 360 ata gtt cac atc ttt gga aaa gtg atc ctg ggc gtc ata gcc gac ttg      1576
Ile Val His Ile Phe Gly Lys Val Ile Leu Gly Val Ile Ala Asp Leu
                365                 370                 375 cct tgc att agt gtt tgg aat gtc ttc ctg ttg gcc aac ttc acc ctt      1624
Pro Cys Ile Ser Val Trp Asn Val Phe Leu Leu Ala Asn Phe Thr Leu
            380                 385                 390 gtc ctc agt att ttt att ctg ccg ttg atg cac acg tac gct ggc ctg      1672
Val Leu Ser Ile Phe Ile Leu Pro Leu Met His Thr Tyr Ala Gly Leu
            395                 400                 405 gcg gtc atc tgt gcg ctg ata ggg ttt tcc agt ggt tat ttc tcc cta      1720
Ala Val Ile Cys Ala Leu Ile Gly Phe Ser Ser Gly Tyr Phe Ser Leu
410                 415                 420 atg ccc gta gtg act gaa gac ttg gtt ggc att gaa cac ctg gcc aat      1768
Met Pro Val Val Thr Glu Asp Leu Val Gly Ile Glu His Leu Ala Asn
425                 430                 435                 440 gcc tac ggc atc atc atc tgt gct aat ggc atc tct gca ttg ctg gga      1816
Ala Tyr Gly Ile Ile Ile Cys Ala Asn Gly Ile Ser Ala Leu Leu Gly
                445                 450                 455 cca cct ttt gca ggg tgg atc tat gac atc acg caa aaa tat gat ttt      1864
```

-continued

| | | | | | | | | | | | | | | |
|---|---|---|---|---|---|---|---|---|---|---|---|---|---|---|
|Pro|Pro|Phe|Ala|Gly|Trp|Ile|Tyr|Asp|Ile|Thr|Gln|Lys|Tyr|Asp|Phe|
| | | |460| | | |465| | | |470| | | |

```
tcc ttc tac ata tgt ggt ttg ctt tac atg ata gga ata ctc ttt tta      1912
Ser Phe Tyr Ile Cys Gly Leu Leu Tyr Met Ile Gly Ile Leu Phe Leu
        475                 480                 485 ctt att cag ccg tgc att cga att ata gaa caa tcc aga aga aaa tac      1960
Leu Ile Gln Pro Cys Ile Arg Ile Ile Glu Gln Ser Arg Arg Lys Tyr
        490                 495                 500 atg gat ggt gca cat gtt tag tatcatgtaa tgttccgtgt aggtttcatt         2011
Met Asp Gly Ala His Val  *
505             510 gtaatactca tgcctacctc gcatggttgc tgtgaggcac ctatgacagg acgtgggaaa    2071
gcattttgta cggtaactgg cactgtcatt tgtaaatgcc attgtcacag cctcatttgt    2131
aagcagcact gcctctctgt ttggggagat gtaatgctgg aagatcttaa ggactacata    2191
cattctagag atgacagtgt tgttcaaaga cagcctagta agtaattggt agaaatgccc    2251
ttataaaaac cattctcttg tcatctactg ggactagggt tttaaataca gcttttaaaa    2311
acaaaaacag ggaataaaag cttttcaact caaccacttc tttgtaagac aaaactgaag    2371
tatctgtgtg cttccagaaa gcttacagat aaatgggttt caagcacaag aatatgacta    2431
gatttcagaa attaattatt acagggagct attgatctac tagcatcaaa caaaggcaag    2491
ctctaattcc acaggtaata caatttagtg caattaaaga aacacggctt gtattttat     2551 gagggaattc tgcagctagg gattgtgact cctaaatcct cctctaaaag aaggcacttg    2611
ccattaatcc taattcagtg ctatccagtt ataaatggaa tcttgagaca aaaccttaac    2671
aaagaaataa cagtaatgat ttccttagca gaagccgtat ttgtacgcac aacattaaat    2731
caagggctac aattcaagca ctttttattcg tatcattggc ctcttagatg atataagcat   2791
gaggtggggc ctgtaatatt ttttctgag tttcttctgc ccaaaaatat aatatagaac     2851
taattgctaa ctgacaaata aagttaatag ttaaatcatc tccaaggaat gttgctaatc    2911
caaagtataa cactatcaat ttgtgaggat aataaatgga atgccattag tgtagatgtc    2971
tgtgccacat ctgacactgg agtagtgata acaaatagcc catctctaga ctctcgtgtt    3031
gttatataga ccattcattt gcctgagcgt ggcacagttt taaaaatagt tctcttgatt    3091
gatttcatac agaagatgac tgtgatccat gacatctaat aatgcccttt ctttatctga    3151
gatgtctatt tttctaagcc aaacgttttt cagactgcag aatgttcttc ccagatcatt    3211
tgaaatttct ggctgcctta cttgtttaca gatagtttaa gactatttaa atttctactc    3271
acaatttgat catcacacac acacaaatcc ttgaatatca ttgccagtgt cttaggtcaa    3331
atttacctaa agtgaataca gcccattctc aattatcctt cacaattaga cgcaggaatg    3391
ctactaggaa ttggaatcaa acaatgccac cccaagcgta attttagcca gcagtttcag   3451
ttatactcaa ccatgtcctt ctgagctgtt aacaagtgat tcaatggaca agttctcttt    3511
ttgttccatc tccattattt cctgctctaa tgtatagtgg gagtggttgt gtaatgaaag    3571
gaccaccaaa ataataaaag gcagctaatg gaaaggagag acaaaagcat ggttaatata    3631
tatacttaat attacctcca atgactcggg aattgcctgt aaattattat agacaataga    3691
ttgcatgtca tactccattt ggttcaacac aacaacctat gtgttatcat tacagctttg    3751
gctgctgtta aagaatccag ctctctattt tgataaagat aatcttaaag ctgaggcaat    3811
gctccctccc ctatctctct ctgtgtaatt taccatagaa ttaggatgat tagattgaaa    3871
cacatgttgt atgtttaaa aactacattg cttcattact ttcattttcc gacaacatca    3931
```

-continued

```
aactaacaag aggcagtgtt aaatatttta aatggtgcta tagccaatgt atttgaatgc    3991
ttgcactgct ggttgtgtat catcaatatg aacttttat ccaatgactc aactctaatt    4051
acatctaagt tagacttgct cacgttcagt ttgtacagtt gtgtgttgac ttactatgtt    4111
ttgaaagtgg tgacttctac cgaatgagtg gaagttccca ttgtcaaaaa aaataaagac    4171
ctgcttgcag tattcatgtt gacaacagag taaaagagaa tactgtaaag aattactgca    4231
aatatttcct gtttatgtta tttgccgttg tttgaagata ttataaaggg ttaattgtat    4291
atttatatca tgtgctttat cgttttcccc tcatgtatcc aagtaatttt tatttacata    4351
caactaaata aatgttgtcc tctttgaaaa aaaaaaaaa aaaaaaaaa aaaaaaggg      4411 gcggccgc                                                              4419
```

<210> SEQ ID NO 2
<211> LENGTH: 510
<212> TYPE: PRT
<213> ORGANISM: homo sapiens

<400> SEQUENCE: 2

```
Met Tyr Thr Ser His Glu Asp Ile Gly Tyr Asp Phe Glu Asp Gly Pro
  1               5                  10                  15

Lys Asp Lys Lys Thr Leu Lys Pro His Pro Asn Ile Asp Gly Gly Trp
             20                  25                  30

Ala Trp Met Met Val Leu Ser Ser Phe Val His Ile Leu Ile Met
         35                  40                  45

Gly Ser Gln Met Ala Leu Gly Val Leu Asn Val Glu Trp Leu Glu Glu
     50                  55                  60

Phe His Gln Ser Arg Gly Leu Thr Ala Trp Val Ser Ser Leu Ser Met
 65                  70                  75                  80

Gly Ile Thr Leu Ile Val Gly Pro Phe Ile Gly Leu Phe Ile Asn Thr
                 85                  90                  95

Cys Gly Cys Arg Gln Thr Ala Ile Ile Gly Gly Leu Val Asn Ser Leu
            100                 105                 110

Gly Trp Val Leu Ser Ala Tyr Ala Ala Asn Val His Tyr Leu Phe Ile
        115                 120                 125

Thr Phe Gly Val Ala Ala Gly Leu Gly Ser Gly Met Ala Tyr Leu Pro
    130                 135                 140

Ala Val Val Met Val Gly Arg Tyr Phe Gln Lys Arg Arg Ala Leu Ala
145                 150                 155                 160

Gln Gly Leu Ser Thr Thr Gly Thr Gly Phe Gly Thr Phe Leu Met Thr
                165                 170                 175

Val Leu Leu Lys Tyr Leu Cys Ala Glu Tyr Gly Trp Arg Asn Ala Met
            180                 185                 190

Leu Ile Gln Gly Ala Val Ser Leu Asn Leu Cys Val Cys Gly Ala Leu
        195                 200                 205

Met Arg Pro Leu Ser Pro Gly Lys Asn Pro Asn Asp Pro Gly Glu Lys
    210                 215                 220

Asp Val Arg Gly Leu Pro Ala His Ser Thr Glu Ser Val Lys Ser Thr
225                 230                 235                 240

Gly Gln Gln Gly Arg Thr Glu Glu Lys Asp Gly Gly Leu Gly Asn Glu
                245                 250                 255

Glu Thr Leu Cys Asp Leu Gln Ala Gln Glu Cys Pro Asp Gln Ala Gly
            260                 265                 270

His Arg Lys Asn Met Cys Ala Leu Arg Ile Leu Lys Thr Val Ser Trp
        275                 280                 285
```

-continued

```
Leu Thr Met Arg Val Arg Lys Gly Phe Glu Asp Trp Tyr Ser Gly Tyr
    290                 295                 300

Phe Gly Thr Ala Ser Leu Phe Thr Asn Arg Met Phe Val Ala Phe Ile
305                 310                 315                 320

Phe Trp Ala Leu Phe Ala Tyr Ser Ser Phe Val Ile Pro Phe Ile His
                325                 330                 335

Leu Pro Glu Ile Val Asn Leu Tyr Asn Leu Ser Glu Gln Asn Asp Val
            340                 345                 350

Phe Pro Leu Thr Ser Ile Ile Ala Ile Val His Ile Phe Gly Lys Val
        355                 360                 365

Ile Leu Gly Val Ile Ala Asp Leu Pro Cys Ile Ser Val Trp Asn Val
    370                 375                 380

Phe Leu Leu Ala Asn Phe Thr Leu Val Leu Ser Ile Phe Ile Leu Pro
385                 390                 395                 400

Leu Met His Thr Tyr Ala Gly Leu Ala Val Ile Cys Ala Leu Ile Gly
                405                 410                 415

Phe Ser Ser Gly Tyr Phe Ser Leu Met Pro Val Val Thr Glu Asp Leu
            420                 425                 430

Val Gly Ile Glu His Leu Ala Asn Ala Tyr Gly Ile Ile Cys Ala
        435                 440                 445

Asn Gly Ile Ser Ala Leu Leu Gly Pro Pro Phe Ala Gly Trp Ile Tyr
    450                 455                 460

Asp Ile Thr Gln Lys Tyr Asp Phe Ser Phe Tyr Ile Cys Gly Leu Leu
465                 470                 475                 480

Tyr Met Ile Gly Ile Leu Phe Leu Leu Ile Gln Pro Cys Ile Arg Ile
                485                 490                 495

Ile Glu Gln Ser Arg Arg Lys Tyr Met Asp Gly Ala His Val
            500                 505                 510

<210> SEQ ID NO 3
<211> LENGTH: 1533
<212> TYPE: DNA
<213> ORGANISM: homo sapiens
<220> FEATURE:
<221> NAME/KEY: CDS
<222> LOCATION: (1)...(1533)

<400> SEQUENCE: 3 atg tat acc agt cat gaa gat att ggg tat gat ttt gaa gat ggc ccc      48
Met Tyr Thr Ser His Glu Asp Ile Gly Tyr Asp Phe Glu Asp Gly Pro
1               5                   10                  15 aaa gac aaa aag aca ctg aag ccc cac cca aac att gat ggc gga tgg      96
Lys Asp Lys Lys Thr Leu Lys Pro His Pro Asn Ile Asp Gly Gly Trp
            20                  25                  30 gct tgg atg atg gtg ctc tcc tct ttc ttt gtg cac atc ctc atc atg     144
Ala Trp Met Met Val Leu Ser Ser Phe Phe Val His Ile Leu Ile Met
        35                  40                  45 ggc tcc cag atg gcc ctg ggt gtc ctc aac gtg gaa tgg ctg gaa gaa     192
Gly Ser Gln Met Ala Leu Gly Val Leu Asn Val Glu Trp Leu Glu Glu
    50                  55                  60 ttc cac cag agc cgc ggc ctg acc gcc tgg gtc agc tcc ctc agc atg     240
Phe His Gln Ser Arg Gly Leu Thr Ala Trp Val Ser Ser Leu Ser Met
65                  70                  75                  80 ggc atc acc ttg ata gtg ggc cct ttc atc ggc ttg ttc att aac acc     288
Gly Ile Thr Leu Ile Val Gly Pro Phe Ile Gly Leu Phe Ile Asn Thr
                85                  90                  95 tgt ggg tgc cgc cag act gcg atc att gga ggg ctc gtc aac tcc ctg     336
```

```
            Cys Gly Cys Arg Gln Thr Ala Ile Ile Gly Gly Leu Val Asn Ser Leu
                        100                 105                 110 ggc tgg gtg ttg agt gcc tat gct gca aac gtg cat tat ctc ttc att         384
Gly Trp Val Leu Ser Ala Tyr Ala Ala Asn Val His Tyr Leu Phe Ile
        115                 120                 125 act ttt gga gtc gca gct ggc ctg ggc agc ggg atg gcc tac ctg cca         432
Thr Phe Gly Val Ala Ala Gly Leu Gly Ser Gly Met Ala Tyr Leu Pro
130                 135                 140 gcg gtg gtc atg gtg ggc agg tat ttc cag aag aga cgc gcc ctc gcc         480
Ala Val Val Met Val Gly Arg Tyr Phe Gln Lys Arg Arg Ala Leu Ala
145                 150                 155                 160 cag ggc ctc agc acc acg ggg acc gga ttc ggt acg ttc cta atg act         528
Gln Gly Leu Ser Thr Thr Gly Thr Gly Phe Gly Thr Phe Leu Met Thr
                165                 170                 175 gtg ctg ctg aag tac ctg tgc gca gag tac ggc tgg agg aat gcc atg         576
Val Leu Leu Lys Tyr Leu Cys Ala Glu Tyr Gly Trp Arg Asn Ala Met
                180                 185                 190 ttg atc caa ggt gcc gtt tcc cta aac ctg tgt gtt tgt ggg gcg ctc         624
Leu Ile Gln Gly Ala Val Ser Leu Asn Leu Cys Val Cys Gly Ala Leu
            195                 200                 205 atg agg ccc ctc tct cct ggt aaa aac cca aac gac cca gga gag aaa         672
Met Arg Pro Leu Ser Pro Gly Lys Asn Pro Asn Asp Pro Gly Glu Lys
210                 215                 220 gat gtg cgt ggc ctg cca gcg cac tcc aca gaa tct gtg aag tca act         720
Asp Val Arg Gly Leu Pro Ala His Ser Thr Glu Ser Val Lys Ser Thr
225                 230                 235                 240 gga cag cag gga aga aca gaa gag aag gat ggt ggg ctc ggg aac gag         768
Gly Gln Gln Gly Arg Thr Glu Glu Lys Asp Gly Gly Leu Gly Asn Glu
                245                 250                 255 gag acc ctc tgc gac ctg caa gcc cag gag tgc ccc gat cag gcc ggg         816
Glu Thr Leu Cys Asp Leu Gln Ala Gln Glu Cys Pro Asp Gln Ala Gly
                260                 265                 270 cac agg aag aac atg tgt gcc ctc cgg att ctg aag act gtc agc tgg         864
His Arg Lys Asn Met Cys Ala Leu Arg Ile Leu Lys Thr Val Ser Trp
            275                 280                 285 ctc acc atg aga gtc agg aag ggc ttc gag gac tgg tat tcg ggc tac         912
Leu Thr Met Arg Val Arg Lys Gly Phe Glu Asp Trp Tyr Ser Gly Tyr
290                 295                 300 ttt ggg aca gcc tct cta ttt aca aat cga atg ttt gta gcc ttt att         960
Phe Gly Thr Ala Ser Leu Phe Thr Asn Arg Met Phe Val Ala Phe Ile
305                 310                 315                 320 ttc tgg gct ttg ttt gca tac agc agc ttt gtc atc ccc ttc att cac        1008
Phe Trp Ala Leu Phe Ala Tyr Ser Ser Phe Val Ile Pro Phe Ile His
                325                 330                 335 ctc cca gaa atc gtc aat ttg tat aac tta tcg gag caa aac gac gtt        1056
Leu Pro Glu Ile Val Asn Leu Tyr Asn Leu Ser Glu Gln Asn Asp Val
                340                 345                 350 ttc cct ctg acg tca att ata gca ata gtt cac atc ttt gga aaa gtg        1104
Phe Pro Leu Thr Ser Ile Ile Ala Ile Val His Ile Phe Gly Lys Val
            355                 360                 365 atc ctg ggc gtc ata gcc gac ttg cct tgc att agt gtt tgg aat gtc        1152
Ile Leu Gly Val Ile Ala Asp Leu Pro Cys Ile Ser Val Trp Asn Val
370                 375                 380 ttc ctg ttg gcc aac ttc acc ctt gtc ctc agt att ttt att ctg ccg        1200
Phe Leu Leu Ala Asn Phe Thr Leu Val Leu Ser Ile Phe Ile Leu Pro
385                 390                 395                 400 ttg atg cac acg tac gct ggc ctg gcg gtc atc tgt gcg ctg ata ggg        1248
Leu Met His Thr Tyr Ala Gly Leu Ala Val Ile Cys Ala Leu Ile Gly
                405                 410                 415
```

```
ttt tcc agt ggt tat ttc tcc cta atg ccc gta gtg act gaa gac ttg      1296
Phe Ser Ser Gly Tyr Phe Ser Leu Met Pro Val Val Thr Glu Asp Leu
            420                 425                 430 gtt ggc att gaa cac ctg gcc aat gcc tac ggc atc atc atc tgt gct      1344
Val Gly Ile Glu His Leu Ala Asn Ala Tyr Gly Ile Ile Ile Cys Ala
            435                 440                 445 aat ggc atc tct gca ttg ctg gga cca cct ttt gca ggg tgg atc tat      1392
Asn Gly Ile Ser Ala Leu Leu Gly Pro Pro Phe Ala Gly Trp Ile Tyr
450                 455                 460 gac atc acg caa aaa tat gat ttt tcc ttc tac ata tgt ggt ttg ctt      1440
Asp Ile Thr Gln Lys Tyr Asp Phe Ser Phe Tyr Ile Cys Gly Leu Leu
465                 470                 475                 480 tac atg ata gga ata ctc ttt tta ctt att cag ccg tgc att cga att      1488
Tyr Met Ile Gly Ile Leu Phe Leu Leu Ile Gln Pro Cys Ile Arg Ile
            485                 490                 495 ata gaa caa tcc aga aga aaa tac atg gat ggt gca cat gtt tag          1533
Ile Glu Gln Ser Arg Arg Lys Tyr Met Asp Gly Ala His Val *
            500                 505                 510

<210> SEQ ID NO 4
<211> LENGTH: 611
<212> TYPE: PRT
<213> ORGANISM: Artificial Sequence
<220> FEATURE:
<223> OTHER INFORMATION: consensus

<400> SEQUENCE: 4

Ser Phe Leu Ile Asn Gly Phe Thr Asp Gly Phe Pro Lys Ser Phe Gly
1               5                   10                  15

Leu Ile Phe Phe Arg Glu Leu Gln Glu Glu Phe Gln Ala Ser Asn Ser
            20                  25                  30

Glu Thr Ser Trp Asp Ser Ile Ser Ile Leu Leu Ala Val Leu Leu
        35                  40                  45

Phe Ala Gly Pro Leu Ala Ser Ile Leu Val Asn Arg Phe Gly Cys Arg
    50                  55                  60

Leu Val Thr Ile Ala Gly Gly Leu Leu Ala Ser Ser Gly Met Val Leu
65                  70                  75                  80

Ala Ser Phe Ala Thr Asn Ile Ser Glu Leu Tyr Leu Thr Phe Gly Val
                85                  90                  95

Ile Thr Gly Leu Gly Phe Ala Phe Ile Tyr Leu Pro Ala Ile Val Ile
            100                 105                 110

Ile Thr Ser Tyr Phe Glu Lys Lys Arg Ser Leu Ala Thr Gly Ile Ala
            115                 120                 125

Val Ala Gly Ser Gly Val Gly Thr Phe Val Leu Ala Pro Leu Asn Pro
    130                 135                 140

Asp Gln Phe Leu Ile Glu Asn Tyr Gly Ser Lys Trp Arg Gly Ala Leu
145                 150                 155                 160

Leu Phe Phe Gly Gly Met Gly Tyr Val Ile Ala Ile Trp Ser Val Ala
                165                 170                 175

Ile Val Leu Asn Cys Cys Ile Ala Gly Ala Leu Phe Arg Pro Leu Pro
            180                 185                 190

Ser Glu Lys Val Lys Gln Thr Lys Leu Ala Lys Ala Glu Glu Pro Lys
            195                 200                 205

Glu Ala Leu Lys Ser Lys Glu Asn Glu Ala Ser Glu Ser Ile Asp Ser
    210                 215                 220

Ile Arg Ser Ala Ala Lys Ala Ile Val Ser Pro Glu Thr Pro Ala Leu
225                 230                 235                 240
```

```
Ser Leu Ser Pro Glu Leu Thr Pro Lys Lys Asp Gln Leu Gln Lys Leu
                245                 250                 255

Leu Lys Thr Ser Arg Thr Arg Ser Ser Asn Gly Ala Lys Leu Leu Asp
            260                 265                 270

Phe Ser Val Leu Lys Asp Ala Arg Gly Phe Leu Leu Tyr Ala Ser Ser
            275                 280                 285

Gly Ser Leu Ala Ser Leu Gly Thr Gln Leu Phe Leu Pro Gly Ser Ile
        290                 295                 300

Phe Leu Val Asn Phe Ala Lys Ser Leu Gly Glu Ser Leu Ser Ser Val
305                 310                 315                 320

Lys Ser Lys Glu Ala Ala Phe Leu Leu Ser Ile Leu Gly Asp Ser Ser
                325                 330                 335

Asp Lys Glu Gly Phe Gly Gly Ile Phe Ala Arg Pro Ala Thr Leu Leu
            340                 345                 350

Ser Phe Leu Gly Phe Val Ala Asn Leu Lys Glu Thr Lys Ser Asn Arg
        355                 360                 365

Pro Val Leu Ile Tyr Leu Leu Ser Leu Cys Ser Ile Val Ala Val Val
    370                 375                 380

Ile Asn Gly Ile Leu Ser Arg Leu Ala Ser Ala Leu Ala Gly Ser Arg
385                 390                 395                 400

Lys Glu Lys Lys Ile Lys Ser Met Ile Asp Lys Ile Glu Leu Lys Ser
                405                 410                 415

Thr Phe Trp Gly Leu Phe Leu Phe Ser Leu Phe Phe Gly Val Gly Phe
            420                 425                 430

Gly Ser Lys Lys Ala Val Val Ile Leu Ala Leu Gly Phe Leu Leu Phe
        435                 440                 445

Ser Ile Leu Tyr Ala Ile Pro Val Val Gly Leu Gln Lys Tyr Ser Ser
    450                 455                 460

Ala Leu Gly Leu Thr Glu Thr Asp Ala Ser Thr Leu Ile Glu Ala Ile
465                 470                 475                 480

Ala Val Leu Asn Ile Ile Gly Arg Pro Leu Ala Gly Leu Leu Ala Asp
                485                 490                 495

Lys Thr Lys Asn Arg Lys Leu Ala Ile Tyr Asn Leu Ser Leu Ile Leu
            500                 505                 510

Cys Gly Leu Phe Val Ala Phe Ala Pro Leu Ala Thr Ile Phe Leu Gly
        515                 520                 525

Leu Ala Phe Tyr Cys Val Leu Phe Gly Ser Ile Val Phe Leu Leu Ala
    530                 535                 540

Tyr Ala Phe Lys Gly Phe Cys Lys Gly Ser Tyr Ile Ala Leu Thr Ser
545                 550                 555                 560

Val Ile Ala Val Asp Leu Thr Gly Leu Asp Lys Leu Ser Asn Ala Phe
                565                 570                 575

Gly Leu Leu Leu Leu Phe Gln Gly Val Ala Thr Leu Val Gly Pro Pro
            580                 585                 590

Ile Ala Gly Leu Leu Lys Asp Leu Thr Gly Ser Tyr Lys Val Ser Phe
        595                 600                 605

Tyr Phe Ala
    610

<210> SEQ ID NO 5
<211> LENGTH: 487
<212> TYPE: PRT
<213> ORGANISM: homo sapiens

<400> SEQUENCE: 5
```

-continued

```
Met Leu Lys Arg Glu Gly Lys Val Gln Pro Tyr Thr Lys Thr Leu Asp
  1               5                  10                  15

Gly Gly Trp Gly Trp Met Ile Val Ile His Phe Phe Leu Val Asn Val
              20                  25                  30

Phe Val Met Gly Met Thr Lys Thr Phe Ala Ile Phe Phe Val Val Phe
              35                  40                  45

Gln Glu Glu Phe Glu Gly Thr Ser Glu Gln Ile Gly Trp Ile Gly Ser
 50                  55                  60

Ile Met Ser Ser Leu Arg Phe Cys Ala Gly Pro Leu Val Ala Ile Ile
 65                  70                  75                  80

Cys Asp Ile Leu Gly Glu Lys Thr Thr Ser Ile Leu Gly Ala Phe Val
              85                  90                  95

Val Thr Gly Gly Tyr Leu Ile Ser Ser Trp Ala Thr Ser Ile Pro Phe
             100                 105                 110

Leu Cys Val Thr Met Gly Leu Leu Pro Gly Leu Gly Ser Ala Phe Leu
             115                 120                 125

Tyr Gln Val Ala Ala Val Val Thr Thr Lys Tyr Phe Lys Lys Arg Leu
130                 135                 140

Ala Leu Ser Thr Ala Ile Ala Arg Ser Gly Met Gly Leu Thr Phe Leu
145                 150                 155                 160

Leu Ala Pro Phe Thr Lys Phe Leu Ile Asp Leu Tyr Asp Trp Thr Gly
             165                 170                 175

Ala Leu Ile Leu Phe Gly Ala Ile Ala Leu Asn Leu Val Pro Ser Ser
             180                 185                 190

Met Leu Leu Arg Pro Ile His Ile Lys Ser Glu Asn Asn Ser Gly Ile
             195                 200                 205

Lys Asp Lys Gly Ser Ser Leu Ser Ala His Gly Pro Glu Ala His Ala
210                 215                 220

Thr Glu Thr His Cys His Glu Thr Glu Ser Thr Ile Lys Asp Ser
225                 230                 235                 240

Thr Thr Gln Lys Ala Gly Leu Pro Ser Lys Asn Leu Thr Val Ser Gln
             245                 250                 255

Asn Gln Ser Glu Glu Phe Tyr Asn Gly Pro Asn Arg Asn Arg Leu Leu
             260                 265                 270

Leu Lys Ser Asp Glu Glu Ser Asp Lys Val Ile Ser Trp Ser Cys Lys
             275                 280                 285

Gln Leu Phe Asp Ile Ser Leu Phe Arg Asn Pro Phe Phe Tyr Ile Phe
             290                 295                 300

Thr Trp Ser Phe Leu Leu Ser Gln Leu Ala Tyr Phe Ile Pro Thr Phe
305                 310                 315                 320

His Leu Val Ala Arg Ala Lys Thr Leu Gly Ile Asp Ile Met Asp Ala
                 325                 330                 335

Ser Tyr Leu Val Ser Val Ala Gly Ile Leu Glu Thr Val Ser Gln Ile
             340                 345                 350

Ile Ser Gly Trp Val Ala Asp Gln Asn Trp Ile Lys Lys Tyr His Tyr
             355                 360                 365

His Lys Ser Tyr Leu Ile Leu Cys Gly Ile Thr Asn Leu Leu Ala Pro
             370                 375                 380

Leu Ala Thr Thr Phe Pro Leu Leu Met Thr Tyr Thr Ile Cys Phe Ala
385                 390                 395                 400

Ile Phe Ala Gly Gly Tyr Leu Ala Leu Ile Leu Pro Val Leu Val Asp
                 405                 410                 415
```

```
Leu Cys Arg Asn Ser Thr Val Asn Arg Phe Leu Gly Leu Ala Ser Phe
            420                 425                 430

Phe Ala Gly Met Ala Val Leu Ser Gly Pro Pro Ile Ala Gly Trp Leu
            435                 440                 445

Tyr Asp Tyr Thr Gln Thr Tyr Asn Gly Ser Phe Tyr Phe Ser Gly Ile
            450                 455                 460

Cys Tyr Leu Leu Ser Ser Val Ser Phe Phe Phe Val Pro Leu Ala Glu
465                 470                 475                 480

Arg Trp Lys Asn Ser Leu Thr
                485

<210> SEQ ID NO 6
<211> LENGTH: 6
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: The amino acid at position 1 can be glu.
<220> FEATURE:
<221> NAME/KEY: VARIANT
<222> LOCATION: 3
<223> OTHER INFORMATION: The amino acid at position 3 can be ser.
<220> FEATURE:
<221> NAME/KEY: VARIANT
<222> LOCATION: 4
<223> OTHER INFORMATION: The amino acid at position 4 can be phe.
<220> FEATURE:
<221> NAME/KEY: VARIANT
<222> LOCATION: 5
<223> OTHER INFORMATION: The amino acid at position 5 can be ala.

<400> SEQUENCE: 6

Asp Gly Gly Trp Gly Trp
1               5

<210> SEQ ID NO 7
<211> LENGTH: 16
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 5
<223> OTHER INFORMATION: The amino acid at position 5 can be lys.
<220> FEATURE:
<221> NAME/KEY: VARIANT
<222> LOCATION: 6
<223> OTHER INFORMATION: The amino acid at position 6 can be leu.
<220> FEATURE:
<221> NAME/KEY: VARIANT
<222> LOCATION: 11
<223> OTHER INFORMATION: The amino acid at position 11 can be ala.
<220> FEATURE:
<221> NAME/KEY: VARIANT
<222> LOCATION: (1)...(16)
<223> OTHER INFORMATION: Xaa = Any Amino Acid

<400> SEQUENCE: 7

Tyr Phe Xaa Lys Arg Arg Xaa Leu Ala Xaa Gly Xaa Ala Xaa Ala Gly
1               5                   10                  15

<210> SEQ ID NO 8
<211> LENGTH: 22
<212> TYPE: PRT
<213> ORGANISM: Artificial Sequence
<220> FEATURE:
```

```
<223> OTHER INFORMATION: consensus
<220> FEATURE:
<221> NAME/KEY: VARIANT
<222> LOCATION: (1)...(22)
<223> OTHER INFORMATION: Xaa = any amino acid

<400> SEQUENCE: 8

Leu Xaa Xaa Xaa Xaa Xaa Xaa Leu Xaa Xaa Xaa Xaa Xaa Xaa Leu Xaa
 1               5                  10                  15

Xaa Xaa Xaa Xaa Xaa Leu
            20
```

25466, A HUMAN TRANSPORTER FAMILY MEMBER AND USES THEREFOR

CROSS-REFERENCES TO RELATED APPLICATIONS

This application claims the benefit of U.S. Provisional Application No. 60/269,072, filed Feb. 15, 2001, the contents of which are incorporated herein by this reference.

BACKGROUND OF THE INVENTION

Cellular membranes serve to differentiate the contents of a cell from the surrounding environment. These membranes may also serve as effective barriers against the unregulated influx of hazardous or unwanted compounds, and the unregulated efflux of desirable compounds. However, the cell does need a supply of desired compounds and removal of waste products. Transport proteins which are embedded (singly or in complexes) in the cellular membrane (reviewed by Oh and Amidon (1999) in *Membrane Transporters as Drug Targets*, ed. Amidon and Sadee, Kluwer Academic/Plenum Publishers, New York, Chapter 1) are major providers of these functions. There are two general classes of membrane transport proteins: channels or pores, and transporters (also known as carriers or permeases). Channels and transporters differ in their translocation mechanisms. Channels are hydrophilic group-lined protein tunnels whose opening by a regulatory event allow free, rapid passage of their charge-, size-, and geometry-selected small ions down their concentration gradients. Transporters specifically and selectively bind the molecules they move, some with and some against their concentration gradients, across membranes. The binding mechanism causes the action of transporters to be slow and saturable.

Transport molecules are specific for a particular target solute or class of solutes, and are also present in one or more specific membranes. Transport molecules localized to the plasma membrane permit an exchange of solutes with the surrounding environment, while transport molecules localized to intracellular membranes (e.g., membranes of the mitochondrion, peroxisome, lysosome, endoplasmic reticulum, nucleus, or vacuole) permit import and export of molecules from organelle to organelle or to the cytoplasm. For example, in the case of the mitochondrion, transporters in the inner and outer mitochondrial membranes permit the import of sugar molecules, calcium ions, and water (among other molecules) into the organelle and the export of newly synthesized ATP to the cytosol.

Transporters can move molecules by two types of processes. In one process, "facilitated diffusion," transporters move molecules with their concentration gradients. In the other process, "active transport," transporters move molecules against their concentration gradients. Active transport to move a molecule against its gradient requires energy. Primary active transporters, such as $Na^+/K^+$ ATPases or ABC transporters use energy from ATP hydrolysis or light, and establish ion gradients and membrane potential energy. Secondary active transporters, such as the $H^+$/peptide transporter, use the pH or ion gradients established by primary active transporters to transport other molecules. In secondary active transport, the transporter uses two separate binding sites to move the primary ion down its concentration gradient to produce the energy to move the secondary solute against its gradient. The coupled solute either travels in the same direction as the primary solute (symport) or in the opposite direction (antiport).

Transporters play important roles in the ability of the cell to regulate homeostasis, to grow and divide, and to communicate with other cells, e.g., to transport signaling molecules, such as hormones, reactive oxygen species, ions, neurotransmitters or vitamins. A wide variety of human diseases and disorders are associated with defects in transporter or other membrane transport molecules, including certain types of liver disorders (e.g., due to defects in transport of long-chain fatty acids (Al Odaib et al. (1998) *New Eng. J. Med.* 339:1752–1757), hyperlysinemia (mitochondrial lysine transport defect (Oyanagi et al. (1986) *Inherit. Metab. Dis.* 9:313–316)), and cataract (Wintour (1997) *Clin. Exp. Pharmacol. Physiol.* 24(1):1–9).

There are over 30 families of secondary transporters, also known as solute carriers or SLC (reviewed by Berger, et al. (2000) in *The Kidney: Physiology and Pathophysiology*, eds. Seldin DW and Giebisch ., Lippincott, Williams & Wilkins, Philadelphia 1:107–138; see also the website maintained by the HUGO gene nomenclature committee, University College London, UK). The SLC families are classified according to the pair of molecules they move. The SLC16 family transports monocarboxylate ions, coupled with the transport of protons.

SUMMARY OF THE INVENTION

The present invention is based, in part, on the discovery of a novel transporter, referred to herein as "25466". The transporter molecule of the invention is homologous to members of the monocarboxylate (MCT) transporter family, and in particular the SLC16 family. The nucleotide sequence of a cDNA encoding 25466 is shown in SEQ ID NO:1, and the amino acid sequence of a 25466 polypeptide is shown in SEQ ID NO:2. In addition, the nucleotide sequence of the coding region is depicted in SEQ ID NO:3.

Accordingly, in one aspect, the invention features a nucleic acid molecule which encodes a 25466 protein or polypeptide, e.g., a biologically active portion of the 25466 protein. In a preferred embodiment, the isolated nucleic acid molecule encodes a polypeptide having the amino acid sequence of SEQ ID NO:2. In other embodiments, the invention provides isolated 25466 nucleic acid molecules having the nucleotide sequence shown in SEQ ID NO:1 or SEQ ID NO:3. In still other embodiments, the invention provides nucleic acid molecules that are sufficiently or substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 25466 protein or an active fragment thereof.

In a related aspect, the invention further provides nucleic acid constructs which include a 25466 nucleic acid molecule described herein. In certain embodiments, the nucleic acid molecules of the invention are operatively linked to native or heterologous regulatory sequences. Also included are vectors and host cells containing the 25466 nucleic acid molecules of the invention e.g., vectors and host cells suitable for producing polypeptides.

In another related aspect, the invention provides nucleic acid fragments suitable as primers or hybridization probes for the detection of 25466-encoding nucleic acids.

In still another related aspect, isolated nucleic acid molecules that are antisense to a 25466 encoding nucleic acid molecule are provided.

In another aspect, the invention features 25466 polypeptides, and biologically active or antigenic fragments thereof that are useful, e.g., as reagents or targets in assays applicable to treatment and diagnosis of transporter-associated or other 25466-associated, -mediated or -related disorders. In another embodiment, the invention provides 25466 polypeptides having a 25466 activity. Preferred polypeptides are 25466 proteins including at least one MCT domain or one, two, three, four, five, six, seven, eight, nine, ten, eleven, preferably twelve transmembrane domains and, preferably, having a 25466 activity, e.g., a 25466 activity as described herein.

In other embodiments, the invention provides 25466 polypeptides, e.g., a 25466 polypeptide having the amino acid sequence shown in SEQ ID NO:2; an amino acid sequence that is sufficiently or substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or SEQ ID NO:3, wherein the nucleic acid encodes a full length 25466 protein or an active fragment thereof.

In a related aspect, the invention further provides nucleic acid constructs which include a 25466 nucleic acid molecule described herein.

In a related aspect, the invention provides 25466 polypeptides or fragments operatively linked to non-25466 polypeptides to form fusion proteins.

In another aspect, the invention features antibodies and antigen-binding fragments thereof, that react with, or more preferably specifically or selectively bind 25466 polypeptides.

In another aspect, the invention provides methods of screening for compounds that modulate the expression or activity of the 25466 polypeptides or nucleic acids.

In still another aspect, the invention provides a process for modulating 25466 polypeptide or nucleic acid expression or activity, e.g., using the compounds identified in the screens described herein. In certain embodiments, the methods involve treatment of conditions related to aberrant activity or expression of the 25466 polypeptides or nucleic acids, such as conditions involving aberrant or deficient transporter, e.g., monocarboxylate transporter function, e.g. neurological disorders, salivary gland disorders, cellular proliferation and/or differentiation disorders, metabolism disorders, lysosomal storage disorders (e.g., mucopolysaccharidosis), cardiovascular disorders, liver disorders, or immune (e.g., inflammatory) disorders.

The invention also provides assays for determining the activity of or the presence or absence of 25466 polypeptides or nucleic acid molecules in a biological sample, including for disease diagnosis.

In a further aspect, the invention provides assays for determining the presence or absence of a genetic alteration in a 25466 polypeptide or nucleic acid molecule, including for disease diagnosis.

Other features and advantages of the invention will be apparent from the following detailed description, and from the claims.

DETAILED DESCRIPTION OF THE INVENTION

Figure 1:
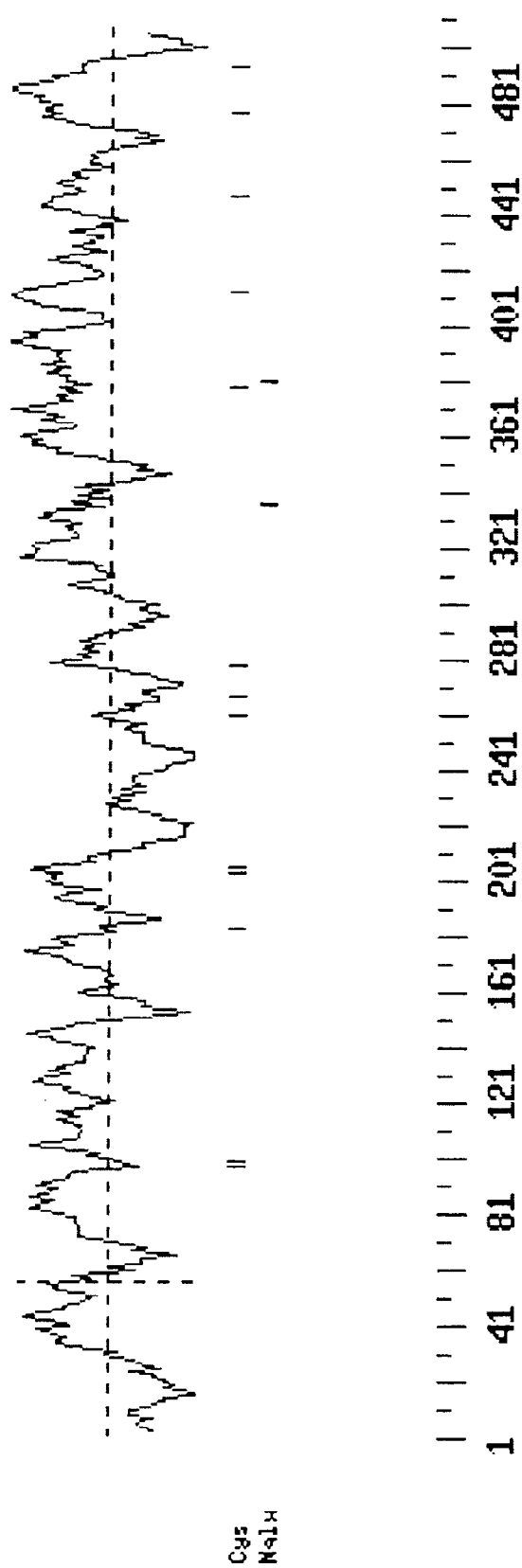
FIG. 1 depicts a hydropathy plot of human 25466. Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human 25466 are indicated. Polypeptides of the invention include fragments which include: all or part of a hydrophobic sequence, e.g., a sequence above the dashed line, e.g., the sequence from about amino acid 73 to 94, from about 352 to 374, and from about 472 to 490 of SEQ ID NO:2; all or part of a hydrophilic sequence, e.g., a sequence below the dashed line, e.g., the sequence from about amino acid 13 to 20, from about 216 to 225, and from about 242 to 250 of SEQ ID NO:2; a sequence which includes a Cys, or a glycosylation site.

The human 25466 sequence (SEQ ID NO:1), which is approximately 4419 nucleotides long including untranslated regions, contains a predicted methionine-initiated coding sequence of about 1533 nucleotides, including the termination codon (nucleotides indicated as coding of SEQ ID NO:1; SEQ ID NO:3). The coding sequence encodes a 510 amino acid protein (SEQ ID NO:2).

Human 25466 contains the following regions or other structural features (for general information regarding PFAM identifiers, PS prefix and PF prefix domain identification numbers, refer to Sonnhammer et at. (1997) *Protein* 28:405–420 or the Pfam website maintained in several locations e.g. by the Sanger Institute (pfam.sanger.ac.uk), Washington University (pfam.wustl.edu), the Karolinska Institute (pfam.cgr.kr.se) or Institut de la National Recherche Agronomique (pfam.jouy.inra.fr)):

A monocarboxylate transporter (MCT) domain (PFAM Accession Number PF01587, SEQ ID NO:4) located at about amino acid residues 40 to 477 of SEQ ID NO:2;

twelve transmembrane domains (predicted by MEMSAT, Jones et al. (1994) *Biochemistry* 33:3038–3049) at about amino acids 33 to 57, 73 to 94, 103 to 119, 126 to 149, 162 to 179, 191 to 209, 315 to 335, 352 to 374, 381 to 399, 406 to 428, 441 to 464, and 472 to 490 of SEQ ID NO:2;

one leucine zipper pattern (Prosite PS00029, SEQ ID NO:8) at about amino acids 387 to 408 of SEQ ID NO:2;

one microbodies C-terminal targeting signal (Prosite PS00342) at about amino acids 508 to 510 of SEQ ID NO:2;

one tyrosine kinase phosphorylation site (Prosite PS00007) at about amino acids 294 to 301 of SEQ ID NO:2;

six protein kinase C phosphorylation sites (Prosite PS00005) at about amino acids 21 to 23, and 236 to 238, 290 to 292, 312 to 314, 467 to 469, and 500 to 502 of SEQ ID NO:2;

two casein kinase II phosphorylation sites (Prosite PS00006) located at about amino acids 3 to 6, and 258 to 261 of SEQ ID NO:2;

two N-glycosylation sites (Prosite PS00001) from about amino acids 345 to 348 and 389 to 392 of SEQ ID NO:2; and nine N-myristoylation sites (Prosite PS00008) from about amino acids 49 to 54, 91 to 96, 98 to 103, 106 to 111, 131 to 136, 137 to 142, 162 to 167, 251 to 256, and 443 to 448 of SEQ ID NO:2.

The 25466 protein contains a significant number of structural characteristics in common with members of the transporter or monocarboxylate (MCT) transporter or SLC16 family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologs of non-human origin, e.g., rat or mouse proteins. Members of a family can also have common functional characteristics.

As used herein, the term "transporter" or "monocarboxylate (MCT) transporter" or "SLC16 family" refers to secondary active transport proteins. Secondary active transporters typically couple the active transport of one molecule, e.g., an ion, e.g., a monocarboxylated ion (e.g., a lactate, pyruvate, acetoacetate, D-β-hydroxybutyrate, acetate, or monocarboxylated monosaccharide ion) against its concentration gradient to the energy gained by concomitant transport of a second molecule, e.g., another ion (e.g., a proton) with its concentration gradient. Monocarboxylate transporters typically participate in the distribution of monocarboxylated ions throughout the body, including monocarboxylated monosaccharides (Havelaar et al. (1998) *J. Biol. Chem.* 273:34568–74) and metabolites from energy utilization pathways (e.g. glucose or fatty acid metabolites, e.g., lactate, pyruvate, acetoacetate, D-β-hydroxybutyrate, acetone, the latter three known collectively as ketone bodies; Berger, et al., supra). A 25466 protein is homologous to a member of the SLC16 family, and in particular a monocarboxylate ion transporter 4 (hMCT4). A GAP alignment to hMCT4 (SwissProt Accession number 015374, SEQ ID NO:5) with the 25466 amino acid sequence (SEQ ID NO:2 showed 25.5% identity and 35.0% similarity between the two sequences (as calculated in matblas from the blosum62.iij matrix).

The monocarboxylate transporter or SLC16 family of proteins is characterized by at least one, two, three, four, five, six, seven, eight, nine, ten, eleven and preferably twelve transmembrane domains which encompass an MCT domain. Typically, the hydrophobic transmembrane domains anchor the transporter within a cell or organelle membrane and through coordinated allosteric movements, effect the transport function across the membrane. The non-transmembrane loops between and beyond the transmembrane domains of the transporter determine the ion binding specificity and provide the ion binding and release activity for the transporter. Typically, the first portion of the monocarboxylate transporters, from the N-terminus through the sixth transmembrane domain, is responsible for proton binding and translocation (Halestrap and Price (1999) *Biochem. J.* 343:281–299), while the remainder is responsible for substrate specificity, binding and translocation. Two regions in the proton translocation portion of the transporter are highly conserved. The first of these, [D/E]G[G/S][W/F][G/A]W (SEQ ID NO:6) can be found in 25466 at about amino acid residues 28 to 33 of SEQ ID NO:2. The second of these, YFXk[R/K][R/L]XlaX[G/A]XaXaG (X can be any amino acid residue, lower case residues are not strictly conserved, SEQ ID NO:7) can be found in 25466 at about amino acid residues 152 to 167 of SEQ ID NO:2.

A 25466 polypeptide can include an "MCT domain" or regions homologous with an "MCT domain". As used herein, the term "MCT domain" includes an amino acid sequence of about 300 to 550 amino acid residues in length and having a bit score for the alignment of the sequence to the MCT domain (HMM) of at least 100. Preferably, the MCT domain includes at least two, three, four, five, six, seven, eight, nine and preferably ten transmembrane domains, and includes a large non-transmembrane loop preferably located between transmembrane domains 6 and 7.

A preferred MCT domain is capable of binding to and/or translocating across a membrane a molecule, e.g., an ion, e.g., a monocarboxylated ion (e.g., a lactate, pyruvate, acetoacetate, D-β-hydroxybutyrate, acetate, or monocarboxylated monosaccharide ion) and a second molecule, e.g., another ion (e.g., a proton). Preferably, an MCT domain includes at least about 350 to 530 amino acids, more preferably about 390 to 500 amino acid residues, or about 420 to 460 amino acids and has a bit score for the alignment of the sequence to the MCT domain (HMM) of at least 120, 150, 180 or greater. The MCT domain (HMM) has been assigned the PFAM Accession Number PF01587 (http://genome.wustl.edu/Pfaml.html). An alignment of the MCT domain (amino acids 40 to 477 of SEQ ID NO:2) of human 25466 with a consensus amino acid sequence (SEQ ID NO:4) derived from a hidden Markov model yielded a bit score of 184.0.

In a preferred embodiment, a 25466 polypeptide or protein has an "MCT domain" or a region which includes at least about 350 to 530 more preferably about 390 to 500 or 420 to 460 amino acid residues and has at least about 60%, 70% 80% 90% 95%, 99%, or 100% homology with an "MCT domain," e.g., the MCT domain of human 25466 (e.g., residues 40 to 477 of SEQ ID NO:2).

To identify the presence of an "MCT" domain in a 25466 protein sequence, and make the determination that a polypeptide or protein of interest has a particular profile, the amino acid sequence of the protein can be searched against the Pfam database of HMMs (e.g., the Pfam database, release 2.1) using the default parameters see the Pfam website maintained in several locations, e.g. by the Sanger Institute (pfam.sanger.ac.uk/Software/Pfam/HMM search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28:405420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference. A search was performed against the HMM database resulting in the identification of an "MCT domain" in the amino acid sequence of human 25466 at about residues 40 to 477 of SEQ ID NO:2.

A 25466 polypeptide can include at least one, two, three, four, five, six, seven, eight, nine, ten, eleven, and preferably twelve "transmembrane domains" or regions homologous with a "transmembrane domains". Likewise, a 25466 polypeptide can include at least one, two, four, eight, preferably thirteen "non-transmembrane regions." As used herein, the term "transmembrane domain" includes an amino acid sequence of about 10 to 40 amino acid residues in length and spans the plasma membrane. Transmembrane domains are rich in hydrophobic residues, e.g., at least 50%, 60%, 70%, 80%, 90%, 95% or more of the amino acids of a transmembrane domain are hydrophobic, e.g., leucines, isoleucines, tyrosines, or tryptophans. Transmembrane domains typically have an alpha-helical structure. Transmembrane domains are described in, for example, Zagotta, W. N. et al., (1996) *Annual Rev. Neurosci.* 19:235–263, the contents of which are incorporated herein by reference.

In a preferred embodiment, a 25466 polypeptide or protein has at least one, two, three, preferably four, five, six, seven, eight, nine, ten, eleven or twelve "transmembrane domains" or regions which include at least about 12 to 35, more preferably about 14 to 30, or 15 to 25 amino acid residues each and have at least about 60%, 70% 80% 90% 95%, 99%, or 100% homology with a "transmembrane domain," e.g., the transmembrane domains of human 25466 (e.g., residues 33 to 57, 73 to 94, 103 to 119, 126 to 149, 162 to 179, 191 to 209, 315 to 335, 352 to 374, 381 to 399, 406 to 428, 441 to 464, and 472 to 490 of SEQ ID NO:2). The transmembrane domains in 25466 are visualized in the hydropathy plot (FIG. 1) as regions mostly above the line for the preferred length of 15 to 25 amino acids.

As used herein, the term "non-transmembrane region" includes an amino acid sequence not identified as a transmembrane domain. The non-transmembrane regions in 25466 include amino acid residues at about 1 to 32, 58 to 72, 95 to 102, 120 to 125, 150 to 161, 180 to 190, 210 to 314, 336 to 351, 375 to 380, 400 to 405, 429 to 440, 465 to 471, and 491 to 510 of SEQ ID NO:2. A 25466 protein can have both the N- and C-termini on the same side of the membrane, e.g., both in the cytoplasm, and a large non-transmembrane region between the sixth and seventh transmembrane domains.

To identify the presence of a "transmembrane" domain in a 25466 protein sequence, and make the determination that a polypeptide or protein of interest has a particular profile, the amino acid sequence of the protein can be analyzed by a transmembrane prediction method that predicts the secondary structure and topology of integral membrane proteins based on the recognition of topological models (MEMSAT, Jones et al., (1994) *Biochemistry* 33:3038–3049).

The 25466 transporter has a leucine zipper motif or regions homologous with a leucine zipper motif. Leucine zippers typically contain a repeat of leucine positioned every seven amino acids (L-x(6)-L-x(6)-L-x(6)-L, Prosite PS00029, SEQ ID NO:8), over a distance of eight helical turns. The segments containing these periodic arrays of leucines appear to exist in an alpha-helical conformation in which leucine side chains extending from one alpha helix interact with those from a similar alpha helix of a second polypeptide, facilitating dimerization. The leucine zipper pattern is present in many gene regulatory proteins, such as CCATT-box and enhancer binding protein (C/EBP), cAMP response element (CRE) binding proteins (CREB, CRE-BP1, ATFs), jun/AP1 family transcription factors, C-myc, L-myc and N-myc oncogenes and octamer-binding transcription factor 2 (Oct-2/OTF-2). These interactions are frequently required for the activity of the protein complex, e.g., transcriptional activation of a nucleic acid via binding to a gene regulatory sequence and subsequent formation of a transcription initiation complex. Leucine zippers therefore mediate protein-protein interactions in vivo and in particular, interactions between multi-subunit transcription factors (homodimers, heterodimers, etc.). The leucine zipper in 25466 transporter can be found at about amino acids 86 to 107 of SEQ ID NO:2.

Thus, in another embodiment, a 25466 transporter or fragment or variant may include one or more activities of a leucine zipper motif, such as binding to another polypeptide that has a leucine zipper, for example, forming a dimer with a 25466 transporter, or fragment or variant thereof containing a leucine zipper. The presence of a leucine zipper indicates that 25466 transporter may participate in different pathways due to an ability to interact with different proteins via the leucine zipper. For example, it may be possible that a leucine zipper motif allows 25466 transporter binding to a protein substrate which it may cleave. The presence of a leucine zipper motif may additionally confer regulation of one or more activities of 25466 transporter modulated through binding to another protein or dissociation from the protein. In any event, it is likely that the leucine zipper modulates or is involved in one or more activities or functions of 25466 transporter through its ability to confer binding of 25466 transporter to a target molecule or binding partner. The term "leucine zipper activity," when used in reference to a protein, means a protein having one or more activities associated with leucine zipper function as described herein or otherwise known in the art.

The 25466 polypeptide can further include a microbody C-terminal targeting signal, or regions homologous with a microbody C-terminal targeting signal. A microbody C-terminal targeting signal typically directs the post-translational import of proteins into microbodies, e.g. peroxisomes, glyosysomes or glycosomes. This sequence, containing a member of each amino acid of the consensus (Prosite PS00342, [STAGCN]-[RKH]-[LIVMAFY]), can be found at about amino acids 508 to 510 of SEQ ID NO:2.

A 25466 family member can include at least one MCT domain, which includes at least one, two, three preferably four, five, six, seven, eight, nine, ten, eleven or twelve transmembrane domains. A 25466 family member can also include at least one preferably four, six, eight, ten or thirteen non-transmembrane regions, including N- and C-terminal segments on the same side of the membrane. Furthermore, a 25466 family member can include at least one leucine zipper motif (PS00029); at least one microbody C-terminal targeting signal (PS00342); at least one, two, four, preferably six protein kinase C phosphorylation sites (PS00005); at least one, preferably two casein kinase II phosphorylation sites (PS00006); at least one tyrosine kinase phosphorylation site (PS00007); at least one, preferably two N-glycosylation sites (PSOOOO1); and at least one, three, six, and preferably nine N-myristoylation sites (PS00008).

As the 25466 polypeptides of the invention can modulate 25466-mediated activities, they can be useful for developing novel diagnostic and therapeutic agents for transporter-associated or other 25466-associated, -mediated or related disorders, as described below.

Monocarboxylate transporters typically transport monocarboxylated metabolites and degradation products across membranes. As metabolite transporters for ions such as lactate, pyruvate, acetoacetate, D-β-hydroxybutyrate, acetate, they play a role in metabolism (Halestrap and Price, supra). As transporters of degradation products, such as monocarboxylated monosaccharides or branched chain oxo-acids derived from leucine, valine and isoleucine (Havelaar et al. (1998) *J. Biol. Chem.* 273:34568–74; Halestrap and Price, supra) they play a role in cell homeostasis, e.g. in lysosomal function. The metabolite transporter role is most prominent in tissues and cells which have high energy demands, such as muscle, heart, brain, fetus via the placenta and tumor cells. Under ischemic conditions, these tissues especially can rely on monocarboxylate transporters to translocate metabolites. The degradation product transporter role is prominent in liver and systemic defects in this transporter function are evident as lysosomal storage diseases which often result in neurodegeneration or mental retardation.

As used herein, a "25466 activity", "biological activity of 25466" or "functional activity of 25466", refers to an activity exerted by a 25466 protein, polypeptide or nucleic acid molecule on e.g., a 25466-responsive cell or on a 25466 substrate, e.g., a protein substrate, as determined in vivo or in vitro. In one embodiment, a 25466 activity is a direct activity, such as an association with a 25466 target molecule. A "target molecule" or "binding partner" is a molecule with which a 25466 protein binds or interacts in nature. In an exemplary embodiment, 25466 is a transporter, e.g., an ion transporter e.g., a monocarboxylate ion transporter, and thus binds to or interacts in nature with a molecule, e.g., an ion, e.g., a monocarboxylated ion (e.g., a lactate, pyruvate, acetoacetate, D-β-hydroxybutyrate, acetate, or monocarboxylated monosaccharide ion) and a second molecule, e.g., an ion (e.g., a proton).

A 25466 activity can also be an indirect activity, e.g., a cellular signaling activity mediated by interaction of the 25466 protein with a 25466 receptor. Based on the above-described sequence structures and similarities to molecules of known function, the 25466 molecules of the present invention have similar biological activities as MCT family members. For example, the 25466 proteins of the present invention can have one or more of the following activities: (1) the ability to reside within a membrane, e.g., a cell membrane, lysosome membrane, or microbody membrane; (2) the ability to interact with, e.g., bind to, a substrate or target molecule; (3) the ability to transport a substrate or target molecule, e.g., an ion (e.g., a monocarboxylated ion, e.g., a lactate, pyruvate, acetoacetate, D-β-hydroxybutyrate, acetate, or monocarboxylated monosaccharide ion) across a membrane; (4) the ability to transport a second substrate or target molecule, e.g., another ion (e.g., a proton) across a membrane; (5) the ability to interact with and/or modulate the activity of a second non-transporter protein; (6) the ability to modulate metabolism; (7) the ability to modulate cellular signaling and/or gene transcription (e.g., either directly or indirectly); or (8) the ability to modulate tissue growth and remodeling, including differentiation and proliferation.

The 25466 molecules of the invention can modulate the activities of cells in tissues where they are expressed. For example, 25466 mRNA has high levels of expression in brain cortex, hypothalamus tissue, and dorsal root ganglion, salivary glands, and differential levels of expression between tumors and their corresponding normal tissue, e.g. a high level of 25466 expression in normal ovary, but only a trace amount in ovary tumor; medium levels of 25466 expression in prostate tumor and breast tumor, but low levels of expression in normal prostate and breast; and medium levels of 25466 expression in colon tumor and lung tumor, but only trace amounts in normal colon and lung. Accordingly, the 25466 molecules of the invention can act as therapeutic or diagnostic agents for neurological disorders, salivary gland disorders, and cellular proliferative and/or differentiative disorders, as well as disorders related to tissues where 25466 mRNA is expressed at lower levels as described below. Medium amounts of 25466 expression also were found in nerve, kidney, congestive heart failure heart tissue, and skin. Small amounts of 25466 expression also were found in normal spinal cord, normal heart, diseased aorta, skeletal muscle, inflammatory bowel disease colon tissue, normal liver, and fibrotic liver. Trace amounts of 25466 expression also were found in normal vein, human umbilical vein endothelial cells, hemangioma tissue, adipose tissue, pancreas, primary osteoblasts, chronic obstructive pulmonary disease lung tissue, normal spleen, normal lymph node, normal tonsil, normal small intestine, synovium, bone marrow monocytes, activated peripheral blood monocytes, and neutrophils.

The 25466 molecules can be used to treat neurological disorders in part because the 25466 mRNA is expressed in brain cortex, hypothalamus tissue, and dorsal root ganglion. Neurological disorders include CNS, cognitive and neurodegenerative disorders, Examples of disorders include, but are not limited to, autonomic function disorders such as hypertension and sleep disorders, and neuropsychiatric disorders, such as depression, schizophrenia, schizoaffective disorder, Korsakoff's psychosis, alcoholism, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans) and other Lewy diffuse body diseases, progressive supranuclear palsy, corticobasal degenration, multiple system atrophy, including striatonigral degenration, Shy-Drager syndrome, and olivopontocerebellar atrophy, and Huntington's disease, senile dementia, Gilles de la Tourette's syndrome, epilepsy, and Jakob-Creutzfieldt disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease. Further CNS-related disorders include, for example, those listed in the American Psychiatric Association's Diagnostic and Statistical manual of Mental Disorders (DSM), the most current version of which is incorporated herein by reference in its entirety.

The 25466 molecules can be used to treat salivary gland disorders in part because the 25466 mRNA is expressed in salivary glands. Salivary gland disorders include, but are not limited to sialadenitis, mumps, xerostomia, Mikulicz's syndrome, sialolithiasis, Rosai-Dorfman disease, lacrimo-auriculodentodigital syndrome, hypoplasia/agenesis of the salivary gland, polycystic-dysgenetic disease of the salivary glands and Wegener's granulomatosis.

The 25466 molecules can be used to treat cellular proliferative and/or differentiative disorders in part because the 25466 mRNA is differentially expressed in tumors relative to their corresponding normal tissue, e.g. a high level of 25466 expression in normal ovary, but only a trace amount in ovary tumor; medium levels of 25466 expression in prostate tumor and breast tumor, but low levels of expression in normal prostate and breast; and medium levels of 25466 expression in colon tumor and lung tumor, but only trace amounts in normal colon and lung. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 25466 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Thus, the 25466 molecules can act as novel diagnostic targets and therapeutic agents for controlling one or more neurological disorders, salivary gland disorders, or cellular proliferation and/or differentiation disorders or other monocarboxylate transporter disorders. As used herein, "monocarboxylate transporter disorders" are diseases or disorders whose pathogenesis is caused by, is related to, or is associated with aberrant or deficient monocarboxylate transporter protein function or expression. Examples of such disorders, e.g., transporter or other 25466-associated disorders, include but are not limited to, cellular proliferation and/or differentiation disorders as described above, as well as, metabolism disorders, lysosomal storage disorders (e.g., mucopolysaccharidosis), cardiovascular disorders, liver disorders, or immune (e.g., inflammatory) disorders.

A 25466 nucleic acid or protein of the invention can play an important role in or can be used to treat metabolic disorders in part because aberrant or deficient function or expression of monocarboxylate transporter family members can result in disorders of metabolism. Diseases of metabolic imbalance include, but are not limited to, mucopolysaccharidosis, obesity, anorexia nervosa, cachexia, lipid disorders, diabetes, ketosis and acidosis.

A 25466 molecule can be used to treat cardiovascular disorders in part because aberrant or deficient function or expression of monocarboxylate transporter family members can result in disorders of the cardiovascular system. Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of cardiovascular disorders include but are not limited to, hypertension, atherosclerosis, coronary artery spasm, coronary artery disease, arrhythmias, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, disorders involving cardiac transplantation, and congestive heart failure. A cardivasular disease or disorder also includes an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

A 25466 molecule can be used to treat liver disorders in part because aberrant or deficient function or expression of monocarboxylate transporter family members can result in disorders of the hepatic system. Disorders which can be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, Al-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein can be used for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

The 25466 nucleic acid or protein of the invention can be used to treat and/or diagnose a variety of immune, e.g., inflammatory, (e.g. respiratory inflammatory) disorders in part because aberrant or deficient function or expression of monocarboxylate transporter family members can result in disorders of the immune system. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 25466 protein, fragments thereof, and derivatives and other variants of the sequence in SEQ ID NO:2 thereof are collectively referred to as "polypeptides or proteins of the invention" or "25466 polypeptides or proteins". Nucleic acid molecules encoding such polypeptides or proteins are collectively referred to as "nucleic acids of the invention" or "25466 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) *John Wiley & Sons, N.Y.,* 6.3.1–6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 25466 protein, preferably a mammalian 25466 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 25466 protein having less than about 30%, 20%, 10% and more preferably 5% (by dry weight), of non-25466 protein (also referred to herein as a "contaminating protein"), or of chemical precursors or non-25466 chemicals. When the 25466 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 25466 (e.g., the sequence of SEQ ID NO:1 or 3) without abolishing or more preferably, without substantially altering a biological activity, whereas an "essential" amino acid residue results in such a change. For example, amino acid residues that are conserved among the polypeptides of the present invention, e.g., those present in the MCT domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 25466 protein is preferably replaced with another amino acid residue from the same side chain family. Alternatively, in another embodiment, mutations can be introduced randomly along all or part of a 25466 coding sequence, such as by saturation mutagenesis, and the resultant mutants can be screened for 25466 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 25466 protein includes a fragment of a 25466 protein which participates in an interaction between a 25466 molecule and a non-25466 molecule. Biologically active portions of a 25466 protein include peptides comprising amino acid sequences sufficiently homologous to or derived from the amino acid sequence of the 25466 protein, e.g., the amino acid sequence shown in SEQ ID NO:2, which include fewer amino acids than the full length 25466 protein, and exhibit at least one activity of a 25466 protein. Typically, biologically active portions comprise a domain or motif with at least one activity of the 25466 protein, e.g., monocarboxylate ion transporter activity. A biologically active portion of a 25466 protein can be a polypeptide which is, for example, 10, 25, 50, 100, 200 or more amino acids in length. Biologically active portions of a 25466 protein can be used as targets for developing agents which modulate a 25466 mediated activity, e.g., monocarboxylate ion transporter activity.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 25466 amino acid sequence of SEQ ID NO:2 having 510 amino acid residues, at least [30%] 153, preferably at least [40%] 204, more preferably at least [50%] 255, even more preferably at least [60%] 306, and even more preferably at least [70%] 357, [80%] 408, or [90%] 459 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48 :444–453 algorithm which has been incorporated into the GAP program in the GCG software package (available at the bioinformatics page of the website maintained by Accelrys, Inc., San Diego, Calif., USA), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frame shift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 25466 nucleic acid molecules of the invention. BLAST protein searches can be performed with the XBLAST program, score=50, wordlength=3 to obtain amino acid sequences homologous to 25466 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. (accessible at the website maintained by National Center for Biotechnology Information, Bethesda, Md., USA).

Particular 25466 polypeptides of the present invention have an amino acid sequence sufficiently identical to the amino acid sequence of SEQ ID NO:2. The term "substantially identical" is used herein to refer to a first amino acid sequence that contains a sufficient or minimum number of identical or equivalent (e.g., with a similar side chain) amino acid residues to a second amino acid sequence such that the first and second amino acid sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as sufficiently or substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences have a common functional activity or encode a common structural polypeptide fold or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 25466 polypeptide described herein, e.g., a full length 25466 protein or a fragment thereof, e.g., a biologically active portion of 25466 protein. Also included is a nucleic acid fragment suitable for use as a hybridization probe, which can be used, e.g., to identify a nucleic acid molecule encoding a polypeptide of the invention, 25466 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human 25466 protein (i.e., "the coding region" of SEQ ID NO:1, as shown in SEQ ID NO:3), as well as 5' untranslated sequences (nucleotides 1 to 448 of SEQ ID NO:1) and 3' untranslated sequences (nucleotides 1983 to 4419 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 40 to 477 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

25466 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 25466 protein, e.g., an immunogenic or biologically active portion of a 25466 protein. A fragment can comprise those nucleotides of SEQ ID NO:1, which encode an MCT domain of human 25466. The nucleotide sequence determined from the cloning of the 25466 gene allows for the generation of probes and primers designed for use in identifying and/or cloning other 25466 family members, or fragments thereof, as well as 25466 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 400 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 25466 nucleic acid fragment can include a sequence corresponding to an MCT domain or a transmembrane domain as described herein.

25466 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an MCT domain located at about amino acid residues 40 to 477 of SEQ ID NO:2; or twelve transmembrane domains located at about amino acids 33 to 57, 73 to 94, 103 to 119, 126 to 149, 162 to 179, 191 to 209, 315 to 335, 352 to 374, 381 to 399, 406 to 428, 441 to 464, and 472 to 490 of SEQ ID NO:2.

In another embodiment a set of primers is provided, e.g., primers suitable for use in a PCR, which can be used to amplify a selected region of a 25466 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: an MCT domain from about amino acid 40 to 477 of SEQ ID NO:2; or a transmembrane domain located at about amino acids 33 to 57, 73 to 94, 103 to 119, 126 to 149, 162 to 179, 191 to 209, 315 to 335, 352 to 374, 381 to 399, 406 to 428, 441 to 464, or 472 to 490 of SEQ ID NO:2.

A nucleic acid fragment can encode an epitope bearing region of a polypeptide described herein.

A nucleic acid fragment encoding a "biologically active portion of a 25466 polypeptide" can be prepared by isolating a portion of the nucleotide sequence of SEQ ID NO:1 or 3, which encodes a polypeptide having a 25466 biological activity (e.g., the biological activities of the 25466 proteins are described herein), expressing the encoded portion of the 25466 protein (e.g., by recombinant expression in vitro) and assessing the activity of the encoded portion of the 25466 protein. For example, a nucleic acid fragment encoding a biologically active portion of 25466 includes an MCT domain, e.g., amino acid residues about 40 to 477 of SEQ ID NO:2. A nucleic acid fragment encoding a biologically active portion of a 25466 polypeptide, can comprise a nucleotide sequence which is greater than 900 or more nucleotides in length.

In preferred embodiments, a nucleic acid includes a nucleotide sequence which is about 300, 600, 900, 1200, 1500, 1800, 2200, 2600, 3000, 3400, 3800, 4100, 4400 or more nucleotides in length and hybridizes under stringent hybridization conditions to a nucleic acid molecule of SEQ ID NO:1 or SEQ ID NO:3.

25466 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 25466 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under stringent conditions, to the nucleotide sequence shown in SEQ ID NO 2 or a fragment of the sequence. Nucleic acid molecules corresponding to orthologs, homologs, and allelic variants of the 25466 cDNAs of the invention can further be isolated by mapping to the same chromosome or locus as the 25466 gene.

Preferred variants include those that are correlated with monocarboxylate ion transporter activity.

Allelic variants of 25466, e.g., human 25466, include both functional and non-functional proteins. Functional allelic variants are naturally occurring amino acid sequence variants of the 25466 protein within a population that maintain (1) the ability to reside within a membrane, e.g., a cell, lysosome or microbody membrane; (2) the ability to interact with, e.g., bind to, a substrate or target molecule; (3) the ability to transport a substrate or target molecule, e.g., an ion, e.g., a monocarboxylated ion, e.g., a lactate, pyruvate, acetoacetate, D-β-hydroxybutyrate, acetate, or monocarboxylated monosaccharide ion, across a membrane; (4) the ability to transport a second substrate or target molecule, e.g., an ion, e.g., a proton across a membrane; (5) the ability to interact with and/or modulate the activity of a second non-transporter protein; (6) the ability to modulate metabolism; (7) the ability to modulate cellular signaling and/or gene transcription (e.g., either directly or indirectly); or (8) the ability to modulate tissue growth and remodeling, including differentiation and proliferation. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 25466, e.g., human 25466, protein within a population that do not have (1) the ability to reside within a membrane, e.g., a cell, lysosome or microbody membrane; (2) the ability to interact with, e.g., bind to, a substrate or target molecule; (3) the ability to transport a substrate or target molecule, e.g., an ion, e.g., a monocarboxylated ion, e.g., a lactate, pyruvate, acetoacetate, D-β-hydroxybutyrate, acetate, or monocarboxylated monosaccharide ion, across a membrane; (4) the ability to transport a second substrate or target molecule, e.g., an ion, e.g., a proton across a membrane; (5) the ability to interact with and/or modulate the activity of a second non-transporter protein; (6) the ability to modulate metabolism; (7) the ability to modulate cellular signaling and/or gene transcription (e.g., either directly or indirectly); or (8) the ability to modulate tissue growth and remodeling, including differentiation and proliferation. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 25466 family members and, thus, which have a nucleotide sequence which differs from the 25466 sequences of SEQ ID NO:1 or SEQ ID NO:3 are intended to be within the scope of the invention.

Antisense Nucleic Acid Molecules, Ribozymes and Modified 25466 Nucleic Acid Molecules In another aspect, the invention features, an isolated nucleic acid molecule which is antisense to 25466. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 25466 coding strand, or to only a portion thereof (e.g., the coding region of human 25466 corresponding to SEQ ID NO:3). In another embodiment, the antisense nucleic acid molecule is antisense to a "non-coding region" of the coding strand of a nucleotide sequence encoding 25466 (e.g., the 5' and 3' untranslated regions).

An antisense nucleic acid can be designed such that it is complementary to the entire coding region of 25466 mRNA, but more preferably is an oligonucleotide which is antisense to only a portion of the coding or noncoding region of 25466 mRNA. For example, the antisense oligonucleotide can be complementary to the region surrounding the translation start site of 25466 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 25466 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

In still another embodiment, an antisense nucleic acid of the invention is a ribozyme. A ribozyme having specificity for a 25466-encoding nucleic acid can include one or more sequences complementary to the nucleotide sequence of a 25466 cDNA disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) Nature 334:585–591). For example, a derivative of a Tetrahymena L-19 IVS RNA can be constructed in which the nucleotide sequence of the active site is complementary to the nucleotide sequence to be cleaved in a 25466-encoding mRNA. See, e.g., Cech et al. U.S. Pat. No. 4,987,071; and Cech et al. U.S. Pat. No. 5,116,742. Alternatively, 25466 mRNA can be used to select a catalytic RNA having a specific ribonuclease activity from a pool of RNA molecules. See, e.g., Bartel, D. and Szostak, J. W. (1993) Science 261:1411–1418.

25466 gene expression can be inhibited by targeting nucleotide sequences complementary to the regulatory region of the 25466 (e.g., the 25466 promoter and/or enhancers) to form triple helical structures that prevent transcription of the 25466 gene in target cells. See generally, Helene, C. (1991) Anticancer Drug Des. 6:569–84; Helene, C. (1992) Ann. N.Y. Acad. Sci. 660:27–36; and Maher, L. J. (1992) Bioassays 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 25466 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et a.l (1996) Proc. Natl. Acad. Sci. 93: 14670–675.

PNAs of 25466 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 25466 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al.

(1987) *Proc. Natl. Acad. Sci. USA* 84:64814 652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 25466 nucleic acid of the invention, two complementary regions one having a fluorophore and one a quencher such that the molecular beacon is useful for quantitating the presence of the 25466 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 25466 Polypeptides

In another aspect, the invention features, an isolated 25466 protein, or fragment, e.g., a biologically active portion, for use as immunogens or antigens to raise or test (or more generally to bind) anti-25466 antibodies. 25466 protein can be isolated from cells or tissue sources using standard protein purification techniques. 25466 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present in a native cell.

In a preferred embodiment, a 25466 polypeptide has one or more of the following characteristics:

it has the ability to transport a molecule, e.g., an ion, e.g., a monocarboxylated ion (e.g., a lactate, pyruvate, acetoacetate, D-β-hydroxybutyrate, acetate, or monocarboxylated monosaccharide ion);

it has the ability to transport a second molecule, e.g., an ion, e.g., a proton;

it has a molecular weight, e.g., a deduced molecular weight, preferably ignoring any contribution of post translational modifications, amino acid composition or other physical characteristic of SEQ ID NO:2;

it has an overall sequence similarity of at least 60%, preferably at least 70%, more preferably at least 80, 90, or 95%, with a polypeptide of SEQ ID NO:2;

it can be found with high levels of expression in brain cortex, hypothalamus tissue, and dorsal root ganglion, salivary glands, and can have differential levels of expression between tumors and their corresponding normal tissue, e.g. a high level of 25466 expression in normal ovary, but only a trace amount in ovary tumor; medium levels of 25466 expression in prostate tumor and breast tumor, but low levels of expression in normal prostate and breast; and medium levels of 25466 expression in colon tumor and lung tumor, but only trace amounts in normal colon and lung;

it can be found with medium levels of expression in nerve, kidney, congestive heart failure heart tissue, and skin, with small amounts of expression in normal spinal cord, normal heart, diseased aorta, skeletal muscle, inflammatory bowel disease colon tissue, normal liver, and fibrotic liver, and trace amounts of expression in normal vein, human umbilical vein endothelial cells, hemangioma tissue, adipose tissue, pancreas, primary osteoblasts, chronic obstructive pulmonary disease lung tissue, normal spleen, normal lymph node, normal tonsil, normal small intestine, synovium, bone marrow monocytes, activated peripheral blood monocytes, and neutrophils.

it has an MCT domain which is preferably about 70%, 80%, 90% or 95% identical to amino acid residues about 40 to 477 of SEQ ID NO:2; or it has at least one, two, four, preferably six, and most preferably twelve transmembrane domains with at least 70%, 80%, 90% or 95% identity to amino acids about 33 to 57, 73 to 94, 103 to 119, 126 to 149, 162 to 179, 191 to 209, 315 to 335, 352 to 374, 381 to 399, 406 to 428, 441 to 464, and 472 to 490 of SEQ ID NO:2.

In a preferred embodiment the 25466 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the MCT domain at about amino acid residues about 40 to 477 of SEQ ID NO:2. In another embodiment one or more differences are in the MCT domain at about amino acid residues about 40 to 477 of SEQ ID NO:2.

Other embodiments include a protein that contains one or more changes in amino acid sequence, e.g., a change in an amino acid residue which is not essential for activity. Such 25466 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2. In another embodiment, the protein includes fragments or regions homologous to fragments, at least about 70%, 80%, 90%, 95%, 96%, 97%, 98%, 99% or more homologous to a fragment of SEQ ID NO:2. A fragment of an 25466 protein can be a domain, e.g. an MCT domain or a fragment thereof, e.g. about amino acid residues 40 to 160, 161 to 280, 281 to 400, or 341 to 477 of SEQ ID NO:2.

A 25466 protein or fragment is provided which varies from the sequence of SEQ ID NO:2 in regions defined by amino acids about 1 to 32 or 491 to 510 by at least one but by less than 15, 10 or 5 amino acid residues in the protein or fragment but which does not differ from SEQ ID NO:2 in regions defined by amino acids about 33 to 490. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 25466 protein includes an MCT domain. Moreover, other biologically active portions, in which other regions of the protein are deleted, can be prepared by recombinant techniques and evaluated for one or more of the functional activities of a native 25466 protein.

In a preferred embodiment, the 25466 protein has an amino acid sequence shown in SEQ ID NO:2. In other embodiments, the 25466 protein is sufficiently or substantially identical to SEQ ID NO:2. In yet another embodiment, the 25466 protein is sufficiently or substantially identical to SEQ ID NO:2 and retains the functional activity of the protein of SEQ ID NO:2, as described in detail in the subsections above.

25466 Chimeric or Fusion Proteins

In another aspect, the invention provides 25466 chimeric or fusion proteins. As used herein, a 25466 "chimeric protein" or "fusion protein" includes a 25466 polypeptide linked to a non-25466 polypeptide. A "non-25466 polypeptide" refers to a polypeptide having an amino acid sequence corresponding to a protein which is not substantially homologous to the 25466 protein, e.g., a protein which is different from the 25466 protein and which is derived from the same or a different organism. The 25466 polypeptide of the fusion protein can correspond to all or a portion e.g., a fragment described herein of a 25466 amino acid sequence. In a preferred embodiment, a 25466 fusion protein includes at least one (or two) biologically active portion of a 25466 protein. The non-25466 polypeptide can be fused to the N-terminus or C-terminus of the 25466 polypeptide.

The fusion protein can include a moiety which has a high affinity for a ligand. For example, the fusion protein can be a GST-25466 fusion protein in which the 25466 sequences are fused to the C-terminus of the GST sequences. Such fusion proteins can facilitate the purification of recombinant 25466. Alternatively, the fusion protein can be a 25466 protein containing a heterologous signal sequence at its N-terminus. In certain host cells (e.g., mammalian host cells), expression and/or secretion of 25466 can be increased through use of a heterologous signal sequence.

Fusion proteins can include all or a part of a serum protein, e.g., a portion of an immunoglobulin (e.g., IgG, IgA, or IgE), e.g., an Fc region and/or the hinge C1 and C2 sequences of an immunoglobulin or human serum albumin.

The 25466 fusion proteins of the invention can be incorporated into pharmaceutical compositions and administered to a subject in vivo. The 25466 fusion proteins can be used to affect the bioavailability of a 25466 substrate. 25466 fusion proteins can be useful therapeutically for the treatment of disorders caused by, for example, (i) aberrant modification or mutation of a gene encoding a 25466 protein; (ii) mis-regulation of the 25466 gene; and (iii) aberrant post-translational modification of a 25466 protein.

Moreover, the 25466-fusion proteins of the invention can be used as immunogens to produce anti-25466 antibodies in a subject, to purify 25466 ligands and in screening assays to identify molecules which inhibit the interaction of 25466 with a 25466 substrate.

Expression vectors are commercially available that already encode a fusion moiety (e.g., a GST polypeptide). A 25466-encoding nucleic acid can be cloned into such an expression vector such that the fusion moiety is linked in-frame to the 25466 protein.

Variants of 25466 Proteins

In another aspect, the invention also features a variant of a 25466 polypeptide, e.g., which functions as an agonist (mimetics) or as an antagonist. Variants of the 25466 proteins can be generated by mutagenesis, e.g., discrete point mutation, the insertion or deletion of sequences or the truncation of a 25466 protein. An agonist of the 25466 proteins can retain substantially the same, or a subset, of the biological activities of the naturally occurring form of a 25466 protein. An antagonist of a 25466 protein can inhibit one or more of the activities of the naturally occurring form of the 25466 protein by, for example, competitively modulating a 25466-mediated activity of a 25466 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 25466 protein.

Variants of a 25466 protein can be identified by screening combinatorial libraries of mutants, e.g., truncation mutants, of a 25466 protein for agonist or antagonist activity.

Libraries of fragments e.g., N terminal, C terminal, or internal fragments, of a 25466 protein coding sequence can be used to generate a variegated population of fragments for screening and subsequent selection of variants of a 25466 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 25466 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 25466 library. For example, a library of expression vectors can be transfected into a cell line, e.g., a cell line, which ordinarily responds to 25466 in a substrate-dependent manner. The transfected cells are then contacted with 25466 and the effect of the expression of the mutant on signaling by the 25466 substrate can be detected, e.g., by measuring monocarboxylate ion transport, proton transport, pH, or substrate or target molecule binding activity. Plasmid DNA can then be recovered from the cells which score for inhibition, or alternatively, potentiation of signaling by the 25466 substrate, and the individual clones further characterized.

In another aspect, the invention features a method of making a 25466 polypeptide, e.g., a peptide having a non-wild type activity, e.g., an antagonist, agonist, or super agonist of a naturally occurring 25466 polypeptide, e.g., a naturally occurring 25466 polypeptide. The method includes altering the sequence of a 25466 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 25466 polypeptide a biological activity of a naturally occurring 25466 polypeptide. The method includes altering the sequence, e.g., by substitution or deletion of one or more residues, of a 25466 polypeptide, e.g., altering the sequence of a non-conserved region, or a domain or residue described herein, and testing the altered polypeptide for the desired activity.

Anti-25466 Antibodies

In another aspect, the invention provides an anti-25466 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 25466 protein or, antigenic peptide fragment of 25466 can be used as an immunogen or can be used to identify anti-25466 antibodies made with other immunogens, e.g., cells, membrane preparations, and the like. The antigenic peptide of 25466 should include at least 8 amino acid residues of the amino acid sequence shown in SEQ ID NO:2 and encompasses an epitope of 25466. Preferably, the antigenic peptide includes at least 10 amino acid residues, more preferably at least 15 amino acid residues, even more preferably at least 20 amino acid residues, and most preferably at least 30 amino acid residues.

Fragments of 25466 which include residues about 13 to 20, from about 216 to 225, and from about 242 to 250 of SEQ ID NO:2 can be used to make, e.g., used as immunogens or used to characterize the specificity of an antibody, antibodies against hydrophilic regions of the 25466 protein (see FIG. 1). Similarly, fragments of 25466 which include residues about 73 to 94, about 352 to 374, or about 472 to 490 of SEQ ID NO:2 can be used to make an antibody against a hydrophobic region of the 25466 protein; fragments of 25466 which include residues about 58 to 72, about 180 to 190, or about 336 to 351 can be used to make an antibody against an extracellular region of the 25466 protein; fragments of 25466 which include residues about 1 to 32, about 210 to 314, or about 429 to 440 can be used to make an antibody against an intracellular region of the 25466 protein; fragments of 25466 which include residues about 40 to 477, about 60 to 100, or about 200 to 400 can be used to make an antibody against the MCT region of the 25466 protein.

Antibodies reactive with, or specific or selective for, any of these regions, or other regions or domains described herein are provided.

Preferred epitopes encompassed by the antigenic peptide are regions of 25466 are located on the surface of the protein, e.g., hydrophilic regions, as well as regions with high antigenicity. For example, an Emini surface probability analysis of the human 25466 protein sequence can be used to indicate the regions that have a particularly high probability of being localized to the surface of the 25466 protein and are thus likely to constitute surface residues useful for targeting antibody production.

In a preferred embodiment the antibody can bind to the extracellular portion of the 25466 protein, e.g., it can bind to a whole cell which expresses the 25466 protein. In another embodiment, the antibody binds an intracellular portion of the 25466 protein.

In a preferred embodiment the antibody binds an epitope on any domain or region on 25466 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125, 023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80: 1553–1559); Morrison, S. L. (1985) Science 229:1202–1207; Oi et al. (1986) BioTechniques 4:214; Winter U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899–903).

The anti-25466 antibody can be a single chain antibody. A single-chain antibody (scFV) can be engineered (see, for example, Colcher, D. et al. (1999) Ann. N Y Acad. Sci. 880:263–80; and Reiter, Y. (1996) Clin. Cancer Res. 2:245–52). The single chain antibody can be dimerized or multimerized to generate multivalent antibodies having specificities for different epitopes of the same target 25466 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208, 020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-25466 antibody (e.g., monoclonal antibody) can be used to isolate 25466 by standard techniques, such as affinity chromatography or immunoprecipitation. Moreover, an anti-25466 antibody can be used to detect 25466 protein (e.g., in a cellular lysate or cell supernatant) in order to evaluate the abundance and pattern of expression of the protein. Anti-25466 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 25466 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 25466 proteins, mutant forms of 25466 proteins, fusion proteins, and the like).

The recombinant expression vectors of the invention can be designed for expression of 25466 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 25466 activity assays, (e.g., direct assays or competitive assays described in detail below), or to generate antibodies specific or selective for 25466 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 25466 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., (1986) *Reviews—Trends in Genetics* 1:1.

Another aspect the invention provides a host cell which includes a nucleic acid molecule described herein, e.g., a 25466 nucleic acid molecule within a recombinant expression vector or a 25466 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 25466 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 25466 protein. Accordingly, the invention further provides methods for producing a 25466 protein using the host cells of the invention. In one embodiment, the method includes culturing the host cell of the invention (into which a recombinant expression vector encoding a 25466 protein has been introduced) in a suitable medium such that a 25466 protein is produced. In another embodiment, the method further includes isolating a 25466 protein from the medium or the host cell.

In another aspect, the invention features, a cell or purified preparation of cells which include a 25466 transgene, or which otherwise misexpress 25466. The cell preparation can consist of human or non-human cells, e.g., rodent cells, e.g., mouse or rat cells, rabbit cells, or pig cells. In preferred embodiments, the cell or cells include a 25466 transgene, e.g., a heterologous form of a 25466, e.g., a gene derived from humans (in the case of a non-human cell). The 25466 transgene can be misexpressed, e.g., overexpressed or underexpressed. In other preferred embodiments, the cell or cells include a gene which misexpresses an endogenous 25466, e.g., a gene the expression of which is disrupted, e.g., a knockout. Such cells can serve as a model for studying disorders which are related to mutated or misexpressed 25466 alleles or for use in drug screening.

In another aspect, the invention features, a human cell, e.g., a hematopoietic stem cell, transformed with nucleic acid which encodes a subject 25466 polypeptide.

Also provided are cells, preferably human cells, e.g., human hematopoietic or fibroblast cells, in which an endogenous 25466 is under the control of a regulatory sequence that does not normally control the expression of the endogenous 25466 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 25466 gene. For example, an endogenous 25466 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 25466 protein and for identifying and/or evaluating modulators of 25466 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 25466 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 25466 protein to particular cells. A transgenic founder animal can be identified based upon the presence of a 25466 transgene in its genome and/or expression of 25466 mRNA in tissues or cells of the animals. A transgenic founder animal can then be used to breed additional animals carrying the transgene. Moreover, transgenic animals carrying a transgene encoding a 25466 protein can further be bred to other transgenic animals carrying other transgenes.

25466 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.
Uses The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 25466 protein (e.g., via a recombinant expression vector in a host cell in gene therapy applications), to detect a 25466 mRNA (e.g., in a biological sample) or a genetic alteration in a 25466 gene, and to modulate 25466 activity, as described further below. The 25466 proteins can be used to treat disorders characterized by insufficient or excessive production of a 25466 substrate or production of 25466 inhibitors. In addition, the 25466 proteins can be used to screen for naturally occurring 25466 substrates, to screen for drugs or compounds which modulate 25466 activity, as well as to treat disorders characterized by insufficient or excessive production of 25466 protein or production of 25466 protein forms which have decreased, aberrant or unwanted activity compared to 25466 wild type protein (e.g., monocarboxylate transporter function, e.g. neurological disorders, salivary gland disorders, cellular proliferation and/or differentiation disorders, metabolism disorders, lysosomal storage disorders (e.g., mucopolysaccharidosis), cardiovascular disorders, liver disorders, or immune (e.g., inflammatory) disorders.). Moreover, the anti-25466 antibodies of the invention can be used to detect and isolate 25466 proteins, regulate the bioavailability of 25466 proteins, and modulate 25466 activity.

A method of evaluating a compound for the ability to interact with, e.g., bind, a subject 25466 polypeptide is provided. The method includes: contacting the compound with the subject 25466 polypeptide; and evaluating ability of the compound to interact with, e.g., to bind or form a complex with the subject 25466 polypeptide. This method can be performed in vitro, e.g., in a cell free system, or in vivo, e.g., in a two-hybrid interaction trap assay. This method can be used to identify naturally occurring molecules which interact with subject 25466 polypeptide. It can also be used to find natural or synthetic inhibitors of subject 25466 polypeptide. Screening methods are discussed in more detail below.
Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 25466 proteins, have a stimulatory or inhibitory effect on, for example, 25466 expression or 25466 activity, or have a stimulatory or inhibitory effect on, for example, the expression or activity of a 25466 substrate. Compounds thus identified can be used to modulate the activity of target gene products (e.g., 25466 genes) in a therapeutic protocol, to elaborate the biological function of the target gene product, or to identify compounds that disrupt normal target gene interactions.

In one embodiment, the invention provides assays for screening candidate or test compounds which are substrates of a 25466 protein or polypeptide or a biologically active portion thereof. In another embodiment, the invention provides assays for screening candidate or test compounds which bind to or modulate the activity of a 25466 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909–13; Erb et al. (1994) *Proc. Natl. Acad. Sci. USA* 91:11422–426; Zuckermann et al. (1994). *J. Med. Chem.* 37:2678–85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233–51.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 25466 protein or biologically active portion thereof is contacted with a test compound, and the ability of the test compound to modulate 25466 activity is determined. Determining the ability of the test compound to modulate 25466 activity can be accomplished by monitoring, for example, monocarboxylate ion transport. The cell, for example, can be of mammalian origin, e.g., human.

The ability of the test compound to modulate 25466 binding to a compound, e.g., a 25466 substrate, or to bind to 25466 can also be evaluated. This can be accomplished, for example, by coupling the compound, e.g., the substrate, with a radioisotope or enzymatic label such that binding of the compound, e.g., the substrate, to 25466 can be determined by detecting the labeled compound, e.g., substrate, in a complex. Alternatively, 25466 could be coupled with a radioisotope or enzymatic label to monitor the ability of a test compound to modulate 25466 binding to a 25466 substrate in a complex. For example, compounds (e.g., 25466 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 25466 substrate) to interact with 25466 with or without the labeling of any of the interactants can be evaluated. For example, a microphysiometer can be used to detect the interaction of a compound with 25466 without the labeling of either the compound or the 25466. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 25466.

In yet another embodiment, a cell-free assay is provided in which a 25466 protein or biologically active portion thereof is contacted with a test compound and the ability of the test compound to bind to the 25466 protein or biologically active portion thereof is evaluated. Preferred biologically active portions of the 25466 proteins to be used in assays of the present invention include fragments which participate in interactions with non-25466 molecules, e.g., fragments with high surface probability scores.

Soluble and/or membrane-bound forms of isolated proteins (e.g., 25466 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 25466 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 25466, an anti-25466 antibody or its target molecule to facilitate separation of complexed from uncomplexed forms of one or both of the proteins, as well as to accommodate automation of the assay. Binding of a test compound to a 25466 protein, or interaction of a 25466 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/25466 fusion proteins or glutathione-S-transferase/target fusion proteins can be adsorbed onto glutathione SEPHAROSE™ beads (Sigma Chemical, St. Louis, Mo.) or glutathione derivatized microtiter plates, which are then combined with the test compound or the test compound and either the non-adsorbed target protein or 25466 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 25466 binding or activity determined using standard techniques.

Other techniques for immobilizing either a 25466 protein or a target molecule on matrices include using conjugation of biotin and streptavidin. Biotinylated 25466 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 25466 protein or target molecules but which do not interfere with binding of the 25466 protein to its target molecule. Such antibodies can be derivatized to the wells of the plate, and unbound target or 25466 protein trapped in the wells by antibody conjugation. Methods for detecting such complexes, in addition to those described above for the GST-immobilized complexes, include immunodetection of complexes using antibodies reactive with the 25466 protein or target molecule, as well as enzyme-linked assays which rely on detecting an enzymatic activity associated with the 25466 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. (1999) *Current Protocols in Molecular Biology*, J. Wiley, New York.); and immunoprecipitation (see, for example, Ausubel, F. et al., eds. (1999) *Current Protocols in Molecular Biology*, J. Wiley, New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl.* 699:499–525). Further, fluorescence energy transfer can also be conveniently utilized, as described herein, to detect binding without further purification of the complex from solution.

In a preferred embodiment, the assay includes contacting the 25466 protein or biologically active portion thereof with a known compound which binds 25466 to form an assay mixture, contacting the assay mixture with a test compound, and determining the ability of the test compound to interact with a 25466 protein, wherein determining the ability of the test compound to interact with a 25466 protein includes determining the ability of the test compound to preferentially bind to 25466 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 25466 genes herein identified. In an alternative embodiment, the invention provides methods for determining the ability of the test compound to modulate the activity of a 25466 protein through modulation of the activity of a downstream effector of a 25466 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 25466 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 25466 ("25466-binding proteins" or "25466-bp") and are involved in 25466 activity. Such 25466-bps can be activators or inhibitors of signals by the 25466 proteins or 25466 targets as, for example, downstream elements of a 25466-mediated signaling pathway.

The two-hybrid system is based on the modular nature of most transcription factors, which consist of separable DNA-binding and activation domains. Briefly, the assay utilizes two different DNA constructs. In one construct, the gene that codes for a 25466 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 25466 protein can be the fused to the activator domain.) If the "bait" and the "prey" proteins are able to interact, in vivo, forming a 25466-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 25466 protein.

In another embodiment, modulators of 25466 expression are identified. For example, a cell or cell free mixture is contacted with a candidate compound and the expression of 25466 mRNA or protein evaluated relative to the level of expression of 25466 mRNA or protein in the absence of the candidate compound. When expression of 25466 mRNA or protein is greater in the presence of the candidate compound than in its absence, the candidate compound is identified as a stimulator of 25466 mRNA or protein expression. Alternatively, when expression of 25466 mRNA or protein is less (statistically significantly less) in the presence of the candidate compound than in its absence, the candidate compound is identified as an inhibitor of 25466 mRNA or protein expression. The level of 25466 mRNA or protein expression can be determined by methods described herein for detecting 25466 mRNA or protein.

In another aspect, the invention pertains to a combination of two or more of the assays described herein. For example, a modulating agent can be identified using a cell-based or a cell free assay, and the ability of the agent to modulate the activity of a 25466 protein can be confirmed in vivo, e.g., in an animal such as an animal model for a monocarboxylate transporter function, e.g. an animal with a neurological disorder, salivary gland disorder, cellular proliferation and/or differentiation disorder, metabolism disorder, lysosomal storage disorder (e.g., mucopolysaccharidosis), cardiovascular disorder, liver disorder, or immune (e.g., inflammatory) disorder.

This invention further pertains to novel agents identified by the above-described screening assays. Accordingly, it is within the scope of this invention to further use an agent identified as described herein (e.g., a 25466 modulating agent, an antisense 25466 nucleic acid molecule, a 25466-specific antibody, or a 25466-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 25466 with a disease; (ii) identify an individual from a minute biological sample (tissue typing); and (iii) aid in forensic identification of a biological sample. These applications are described in the subsections below.

Chromosome Mapping

The 25466 nucleotide sequences or portions thereof can be used to map the location of the 25466 genes on a chromosome. This process is called chromosome mapping.

Chromosome mapping is useful in correlating the 25466 sequences with genes associated with disease.

Briefly, 25466 genes can be mapped to chromosomes by preparing PCR primers (preferably 15–25 bp in length) from the 25466 nucleotide sequences. These primers can then be used for PCR screening of somatic cell hybrids containing individual human chromosomes. Only those hybrids containing the human gene corresponding to the 25466 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919–924).

Other mapping strategies e.g., in situ hybridization (described in Fan, Y. et al. (1990) Proc. Natl. Acad. Sci. USA, 87:6223–27), pre-screening with labeled flow-sorted chromosomes, and pre-selection by hybridization to chromosome specific cDNA libraries can be used to map 25466 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the 25466 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 25466 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 25466 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 25466 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 25466 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 25466 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 25466 probes can be used to identify tissue by species and/or by organ type.

In a similar fashion, these reagents, e.g., 25466 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 25466.

Such disorders include, e.g., a disorder associated with the misexpression of 25466 gene; a disorder of the nervous system, the cellular proliferative or differentiative system, the salivary gland, the cardiovascular system, the hepatic system, or the inflammatory system.

The method includes one or more of the following:

detecting, in a tissue of the subject, the presence or absence of a mutation which affects the expression of the 25466 gene, or detecting the presence or absence of a mutation in a region which controls the expression of the gene, e.g., a mutation in the 5' control region;

detecting, in a tissue of the subject, the presence or absence of a mutation which alters the structure of the 25466 gene;

detecting, in a tissue of the subject, the misexpression of the 25466 gene, at the mRNA level, e.g., detecting a non-wild type level of a mRNA;

detecting, in a tissue of the subject, the misexpression of the gene, at the protein level, e.g., detecting a non-wild type level of a 25466 polypeptide.

In preferred embodiments the method includes: ascertaining the existence of at least one of: a deletion of one or more nucleotides from the 25466 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 25466 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 25466 gene; the presence of a non-wild type splicing pattern of a messenger RNA transcript of the gene; or a non-wild type level of 25466.

Methods of the invention can be used prenatally or to determine if a subject's offspring will be at risk for a disorder.

In preferred embodiments the method includes determining the structure of a 25466 gene, an abnormal structure being indicative of risk for the disorder.

In preferred embodiments the method includes contacting a sample from the subject with an antibody to the 25466 protein or a nucleic acid, which hybridizes specifically with the gene. These and other embodiments are discussed below.

Diagnostic and Prognostic Assays

The presence, level, or absence of 25466 protein or nucleic acid in a biological sample can be evaluated by obtaining a biological sample from a test subject and contacting the biological sample with a compound or an agent capable of detecting 25466 protein or nucleic acid (e.g., mRNA, genomic DNA) that encodes 25466 protein such that the presence of 25466 protein or nucleic acid is detected in the biological sample. The term "biological sample" includes tissues, cells and biological fluids isolated from a subject, as well as tissues, cells and fluids present within a subject. A preferred biological sample is serum. The level of expression of the 25466 gene can be measured in a number of ways, including, but not limited to: measuring the mRNA encoded by the 25466 genes; measuring the amount of protein encoded by the 25466 genes; or measuring the activity of the protein encoded by the 25466 genes.

The level of mRNA corresponding to the 25466 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 25466 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 25466 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 25466 genes.

The level of mRNA in a sample that is encoded by one of 25466 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-BetaReplicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 25466 gene being analyzed.

In another embodiment, the methods further contacting a control sample with a compound or agent capable of detecting 25466 mRNA, or genomic DNA, and comparing the presence of 25466 mRNA or genomic DNA in the control sample with the presence of 25466 mRNA or genomic DNA in the test sample.

A variety of methods can be used to determine the level of protein encoded by 25466. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 25466 protein in a biological sample in vitro as well as in vivo. In vitro techniques for detection of 25466 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 25466 protein include introducing into a subject a labeled anti-25466 antibody. For example, the antibody can be labeled with a radioactive marker whose presence and location in a subject can be detected by standard imaging techniques.

In another embodiment, the methods further include contacting the control sample with a compound or agent capable of detecting 25466 protein, and comparing the presence of 25466 protein in the control sample with the presence of 25466 protein in the test sample.

The invention also includes kits for detecting the presence of 25466 in a biological sample. For example, the kit can include a compound or agent capable of detecting 25466 protein or mRNA in a biological sample; and a standard. The compound or agent can be packaged in a suitable container. The kit can further comprise instructions for using the kit to detect 25466 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 25466 expression or activity. As used herein, the term "unwanted" includes an unwanted phenomenon involved in a biological response such as pain or deregulated cell proliferation.

In one embodiment, a disease or disorder associated with aberrant or unwanted 25466 expression or activity is identified. A test sample is obtained from a subject and 25466 protein or nucleic acid (e.g., mRNA or genomic DNA) is evaluated, wherein the level, e.g., the presence or absence, of 25466 protein or nucleic acid is diagnostic for a subject having or at risk of developing a disease or disorder associated with aberrant or unwanted 25466 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 25466 expression or activity. For example, such methods can be used to determine whether a subject can be effectively treated with an agent for a cell monocarboxylate transporter disorder, e.g. a neurological disorder, a salivary gland disorder, a cellular proliferation and/or differentiation disorder, a metabolism disorder, a lysosomal storage disorder (e.g., mucopolysaccharidosis), a cardiovascular disorder, a liver disorder, or an immune (e.g., inflammatory) disorder.

The methods of the invention can also be used to detect genetic alterations in a 25466 gene, thereby determining if a subject with the altered gene is at risk for a disorder characterized by misregulation in 25466 protein activity or nucleic acid expression, such as a monocarboxylate transporterdisorder, e.g. a neurological disorder, a salivary gland disorder, a cellular proliferation and/or differentiation disorder, a metabolism disorder, a lysosomal storage disorder (e.g., mucopolysaccharidosis), a cardiovascular disorder, a liver disorder, or an immune (e.g., inflammatory) disorder. In preferred embodiments, the methods include detecting, in a sample from the subject, the presence or absence of a genetic alteration characterized by at least one of an alteration affecting the integrity of a gene encoding a 25466-protein, or the mis-expression of the 25466 gene. For example, such genetic alterations can be detected by ascertaining the existence of at least one of 1) a deletion of one or more nucleotides from a 25466 gene; 2) an addition of one or more nucleotides to a 25466 gene; 3) a substitution of one or more nucleotides of a 25466 gene, 4) a chromosomal rearrangement of a 25466 gene; 5) an alteration in the level of a messenger RNA transcript of a 25466 gene, 6) aberrant modification of a 25466 gene, such as of the methylation pattern of the genomic DNA, 7) the presence of a non-wild type splicing pattern of a messenger RNA transcript of a 25466 gene, 8) a non-wild type level of a 25466-protein, 9) allelic loss of a 25466 gene, and 10) inappropriate post-translational modification of a 25466-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 25466-gene. This method can include the steps of collecting a sample of cells from a subject, isolating nucleic acid (e.g., genomic, mRNA or both) from the sample, contacting the nucleic acid sample with one or more primers which specifically hybridize to a 25466 gene under conditions such that hybridization and amplification of the 25466 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 25466 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 25466 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 25466 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 25466 gene and detect mutations by comparing the sequence of the sample 25466 with the corresponding wild-type (control) sequence. Automated sequencing procedures can be utilized when performing the diagnostic assays (Naeve C. W. et al. (1995) *Biotechniques* 19:448–53), including sequencing by mass spectrometry.

Other methods for detecting mutations in the 25466 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 25466 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 25466 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 25466 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification can also be performed using Taq ligase for amplification (Barany (1991) *Proc. Natl. Acad. Sci USA* 88:189–93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 25466 gene.

Use of 25466 Molecules as Surrogate Markers

The 25466 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 25466 molecules of the invention can be detected, and can be correlated with one or more biological states in vivo. For example, the 25466 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 25466 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 25466 marker) transcription or expression, the amplified marker can be in a quantity which is more readily detectable than the drug itself. Also, the marker can be more easily detected due to the nature of the marker itself; for example, using the methods described herein, anti-25466 antibodies can be employed in an immune-based detection system for a 25466 protein marker, or 25466-specific radiolabeled probes can be used to detect a 25466 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20.

The 25466 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 25466 protein or RNA) for specific tumor markers in a subject, a drug or course of treatment can be selected that is optimized for the treatment of the specific tumor likely to be present in the subject. Similarly, the presence or absence of a specific sequence mutation in 25466 DNA can correlate with a 25466 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-25466 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR™ EL (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gI ycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety can be a protein or polypeptide possessing a desired biological activity. Such proteins can include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 25466 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 25466 molecules of the present invention or 25466 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 25466 expression or activity, by administering to the subject a 25466 or an agent which modulates 25466 expression or at least one 25466 activity. Subjects at risk for a disease which is caused or contributed to by aberrant or unwanted 25466 expression or activity can be identified by, for example, any or a combination of diagnostic or prognostic assays as described herein. Administration of a prophylactic agent can occur prior to the manifestation of symptoms characteristic of the 25466 aberrance, such that a disease or disorder is prevented or, alternatively, delayed in its progression. Depending on the type of 25466 aberrance, for example, a 25466, 25466 agonist or 25466 antagonist agent can be used for treating the subject. The appropriate agent can be determined based on screening assays described herein.

It is possible that some 25466 disorders can be caused, at least in part, by an abnormal level of gene product, or by the presence of a gene product exhibiting abnormal activity. As such, the reduction in the level and/or activity of such gene products would bring about the amelioration of disorder symptoms.

The 25466 molecules can act as novel diagnostic targets and therapeutic agents for controlling one or more of, monocarboxylate transporter disorders e.g. neurological disorders, salivary gland disorders, cellular proliferation and/or differentiation disorders, metabolism disorders, lysosomal storage disorders (e.g., mucopolysaccharidosis), cardiovascular disorders, liver disorders, or immune (e.g., inflammatory) disorders, all of which are described above. The molecules of the invention also can act as novel diagnostic targets and therapeutic agents for controlling one or more of disorders associated with bone metabolism, viral diseases, or pain disorders.

Aberrant expression and/or activity of 25466 molecules can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by 25466 molecules effects in bone cells, e.g. osteoclasts and osteoblasts, that can in turn result in bone formation and degeneration. For example, 25466 molecules can support different activities of bone resorbing osteoclasts such as the stimulation of differentiation of monocytes and mononuclear phagocytes into osteoclasts. Accordingly, 25466 molecules that modulate the production of bone cells can influence bone formation and degeneration, and thus can be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 25466 molecules can play an important role in the etiology of certain viral diseases, including but not limited to Hepatitis B, Hepatitis C and Herpes Simplex Virus (HSV). Modulators of 25466 activity could be used to control viral diseases. The modulators can be used in the treatment and/or diagnosis of viral infected tissue or virus-associated tissue fibrosis, especially liver and liver fibrosis. Also, 25466 modulators can be used in the treatment and/or diagnosis of virus-associated carcinoma, especially hepatocellular cancer.

Additionally, 25466 can play an important role in the regulation of pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 25466 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 25466 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 25466 expression is through the use of aptamer molecules specific for 25466 protein. Aptamers are nucleic acid molecules having a tertiary structure which permits them to specifically or selectively bind to protein ligands (see, e.g., Osborne, et al. (1997) Curr. Opin. Chem Biol. 1: 5–9; and Patel, D. J. (1997) Curr Opin Chem Biol 1:32–46). Since nucleic acid molecules can in many cases be more conveniently introduced into target cells than therapeutic protein molecules can be, aptamers offer a method by which 25466 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 25466 disorders. For a description of antibodies, see the Antibody section above.

In circumstances wherein injection of an animal or a human subject with a 25466 protein or epitope for stimulating antibody production is harmful to the subject, it is possible to generate an immune response against 25466 through the use of anti-idiotypic antibodies (see, for example, Herlyn, D. (1999) Ann Med 31:66–78; and Bhattacharya-Chatterjee, M., and Foon, K. A. (1998) Cancer Treat Res. 94:51–68). If an anti-idiotypic antibody is introduced into a mammal or human subject, it should stimulate the production of anti-anti-idiotypic antibodies, which should be specific to the 25466 protein. Vaccines directed to a disease characterized by 25466 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) Proc. Natl. Acad. Sci. USA 90:7889–7893).

The identified compounds that inhibit target gene expression, synthesis and/or activity can be administered to a patient at therapeutically effective doses to prevent, treat or ameliorate 25466 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 25466 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) Current Opinion in Biotechnology 7:89–94 and in Shea, K. J. (1994) Trends in Polymer Science 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) Nature 361:645–647. Through the use of isotope-labeling, the "free" concentration of compound which modulates the expression or activity of 25466 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) Analytical Chemistry 67:2142–2144.

Another aspect of the invention pertains to methods of modulating 25466 expression or activity for therapeutic purposes. Accordingly, in an exemplary embodiment, the modulatory method of the invention involves contacting a cell with a 25466 or agent that modulates one or more of the activities of 25466 protein activity associated with the cell. An agent that modulates 25466 protein activity can be an agent as described herein, such as a nucleic acid or a protein, a naturally-occurring target molecule of a 25466 protein (e.g., a 25466 substrate or receptor), a 25466 antibody, a 25466 agonist or antagonist, a peptidomimetic of a 25466 agonist or antagonist, or other small molecule.

In one embodiment, the agent stimulates one or 25466 activities. Examples of such stimulatory agents include active 25466 protein and a nucleic acid molecule encoding 25466. In another embodiment, the agent inhibits one or more 25466 activities. Examples of such inhibitory agents include antisense 25466 nucleic acid molecules, anti25466 antibodies, and 25466 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 25466 protein or nucleic acid molecule. In one embodiment, the method involves administering an agent (e.g., an agent identified by a screening assay described herein), or combination of agents that modulates (e.g., up regulates or down regulates) 25466 expression or activity. In another embodiment, the method involves administering a 25466 protein or nucleic acid molecule as therapy to compensate for reduced, aberrant, or unwanted 25466 expression or activity.

Stimulation of 25466 activity is desirable in situations in which 25466 is abnormally downregulated and/or in which increased 25466 activity is likely to have a beneficial effect. For example, stimulation of 25466 activity is desirable in situations in which a 25466 is downregulated and/or in which increased 25466 activity is likely to have a beneficial effect. Likewise, inhibition of 25466 activity is desirable in situations in which 25466 is abnormally upregulated and/or in which decreased 25466 activity is likely to have a beneficial effect.

Pharmacogenomics

The 25466 molecules of the present invention, as well as agents, or modulators which have a stimulatory or inhibitory effect on 25466 activity (e.g., 25466 gene expression) as identified by a screening assay described herein can be administered to individuals to treat (prophylactically or therapeutically) 25466 associated disorders (e.g., monocarboxylate transporter, metabolisc disorders, lysosomal storage, or cellular proliferation or differentiation disorders) associated with aberrant or unwanted 25466 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 25466 molecule or 25466 modulator as well as tailoring the dosage and/or therapeutic regimen of treatment with a 25466 molecule or 25466 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 25466 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 25466 molecule or 25466 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 25466 molecule or 25466 modulator, such as a modulator identified by one of the exemplary screening assays described herein.

The present invention further provides methods for identifying new agents, or combinations, that are based on identifying agents that modulate the activity of one or more of the gene products encoded by one or more of the 25466 genes of the present invention, wherein these products can be associated with resistance of the cells to a therapeutic agent. Specifically, the activity of the proteins encoded by the 25466 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 25466 protein can be applied in clinical trials. For example, the effectiveness of an agent determined by a screening assay as described herein to increase 25466 gene expression, protein levels, or upregulate 25466 activity, can be monitored in clinical trials of subjects exhibiting decreased 25466 gene expression, protein levels, or downregulated 25466 activity. Alternatively, the effectiveness of an agent determined by a screening assay to decrease 25466 gene expression, protein levels, or downregulate 25466 activity, can be monitored in clinical trials of subjects exhibiting increased 25466 gene expression, protein levels, or upregulated 25466 activity. In such clinical trials, the expression or activity of a 25466 gene, and preferably, other genes that have been implicated in, for example, a transporter-associated or another 25466-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 25466 or from a cell or subject in which a 25466 mediated response has been elicited; contacting the array with a 25466 nucleic acid (preferably purified), a 25466 polypeptide (preferably purified), or an anti-25466 antibody, and thereby evaluating the plurality of capture probes. Binding, e.g., in the case of a nucleic acid, hybridization with a capture probe at an address of the plurality, is detected, e.g., by a signal generated from a label attached to the 25466 nucleic acid, polypeptide, or antibody.

The capture probes can be a set of nucleic acids from a selected sample, e.g., a sample of nucleic acids derived from a control or non-stimulated tissue or cell.

The method can include contacting the 25466 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 25466. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features, a method of analyzing 25466, e.g., analyzing structure, function, or relatedness to other nucleic acid or amino acid sequences. The method includes: providing a 25466 nucleic acid or amino acid sequence; comparing the 25466 sequence with one or more preferably a plurality of sequences from a collection of sequences, e.g., a nucleic acid or protein sequence database; to thereby analyze 25466.

The method can include evaluating the sequence identity between a 25466 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 25466. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 25466 molecules are provided in a variety of mediums to facilitate use thereof. A sequence can be provided as a manufacture, other than an isolated nucleic acid or amino acid molecule, which contains a 25466 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 25466 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 25466 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 25466 sequence information.

A variety of data storage structures are available to a skilled artisan for creating a computer readable medium having recorded thereon a 25466 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 25466 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a transporter-associated or another 25466-associated disease or disorder or a pre-disposition to a transporter-associated or another 25466-associated disease or disorder, wherein the method comprises the steps of determining 25466 sequence information associated with the subject and based on the 25466 sequence information, determining whether the subject has a transporter-associated or another 25466-associated disease or disorder and/or recommending a particular treatment for the disease, disorder, or pre-disease condition.

The present invention further provides in an electronic system and/or in a network, a method for determining whether a subject has a transporter-associated or another 25466-associated disease or disorder or a pre-disposition to a disease associated with 25466, wherein the method comprises the steps of determining 25466 sequence information associated with the subject, and based on the 25466 sequence information, determining whether the subject has a transporter-associated or another 25466-associated disease or disorder or a pre-disposition to a transporter-associated or another 25466-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a transporter-associated or another 25466-associated disease or disorder or a pre-disposition to a transporter-associated or another 25466-associated disease or disorder, said method comprising the steps of receiving 25466 sequence information from the subject and/or information related thereto, receiving phenotypic information associated with the subject, acquiring information from the network corresponding to 25466 and/or corresponding to a transporter-associated or another 25466-associated disease or disorder, and based on one or more of the phenotypic information, the 25466 information (e.g., sequence information and/or information related thereto), and the acquired information, determining whether the subject has a transporter-associated or another 25466-associated disease or disorder or a pre-disposition to a transporter-associated or another 25466-associated disease or disorder. The method may further comprise the step of recommending a particular treatment for the disease, disorder, or pre-disease condition.

The present invention also provides a business method for determining whether a subject has a transporter-associated or another 25466-associated disease or disorder or a pre-disposition to a transporter-associated or another 25466-associated disease or disorder, said method comprising the steps of receiving information related to 25466 (e.g., sequence information and/or information related thereto), receiving phenotypic information associated with the subject, acquiring information from the network related to 25466 and/or related to a transporter-associated or another 25466-associated disease or disorder, and based on one or more of the phenotypic information, the 25466 information, and the acquired information, determining whether the subject has a transporter-associated or another 25466-associated disease or disorder or a pre-disposition to a transporter-associated or another 25466-associated disease or disorder . The method may further comprise the step of recommending a particular treatment for the disease, disorder, or pre-disease condition.

The invention also includes an array comprising a 25466 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 25466. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a transporter-associated or another 25466-associated disease or disorder, progression of transporter-associated or another 25466-associated disease or disorder, and processes, such a cellular transformation associated with the transporter-associated or another 25466-associated disease or disorder.

The array is also useful for ascertaining the effect of the expression of a gene on the expression of other genes in the same cell or in different cells (e.g., acertaining the effect of 25466 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 25466) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 25466 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 25466 sequence, or record, in computer readable form; comparing a second sequence to the 25466 sequence; thereby analyzing a sequence. Comparison can include comparing to sequences for sequence identity or determining if one sequence is included within the other, e.g., determining if the 25466 sequence includes a sequence being compared. In a preferred embodiment the 25466 or second sequence is stored on a first computer, e.g., at a first site and the comparison is performed, read, or recorded on a second computer, e.g., at a second site. E.g., the 25466 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

The contents of all references, patents and published patent applications cited throughout this application are incorporated herein by reference.

This invention is further illustrated by the following exemplification, which should not be construed as limiting.

EXEMPLIFICATION

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using P-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 25466 expression was measured by TAQMAN™ quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 25466 gene. Each human 25466 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TAQMAN™ Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TAQMAN™ matrix experiments were carried out on an ABI PRISM™ 7700 Sequence Detection System (PE Applied Biosystems). The thermal cycler conditions were as follows: hold for 2 min at 50° C. and 10 min at 95°C., followed by two-step PCR for 40 cycles of 95°°C. for 15 sec followed by 60° C. for 1 min.

The following method was used to quantitatively calculate human 25466 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 25466 gene is normalized by subtracting the Ct value of the β-2 microglobulin gene to obtain a $_\Delta$Ct value using the following formula: $_\Delta Ct = Ct_{human\ 25466} - Ct_{\beta-2\ microglobulin}$. Expression is then calibrated against a cDNA sample showing a comparatively low level of expression of the human 25466 gene. The $_\Delta$Ct value for the calibrator sample is then subtracted from $_\Delta$Ct for each tissue sample according to the following formula: $_{\Delta\Delta}Ct = _\Delta Ct_{sample} - _\Delta Ct_{caibrator}$. Relative expression is then calculated using the arithmetic formula given by $2^{-\Delta\Delta Ct}$. Expression of the target human 25466 gene in each of the tissues tested is then graphically represented as discussed in more detail below.

The results indicate 25466 mRNA has high levels of expression in brain cortex, hypothalamus tissue, and dorsal root ganglion, salivary glands, and differential levels of expression between tumors and their corresponding normal tissue, e.g. a high level of 25466 expression in normal ovary, but only a trace amount in ovary tumor; medium levels of 25466 expression in prostate tumor and breast tumor, but low levels of expression in normal prostate and breast; and medium levels of 25466 expression in colon tumor and lung tumor, but only trace amounts in normal colon and lung. Medium amounts of 25466 expression also were found in nerve, kidney, congestive heart failure heart tissue, and skin. Small amounts of 25466 expression also were found in normal spinal cord, normal heart, diseased aorta, skeletal muscle, inflammatory bowel disease colon tissue, normal liver, and fibrotic liver. Trace amounts of 25466 expression also were found in normal vein, human umbilical vein endothelial cells, hemangioma tissue, adipose tissue, pancreas, primary osteoblasts, chronic obstructive pulmonary disease lung tissue, normal spleen, normal lymph node, normal tonsil, normal small intestine, synovium, bone marrow monocytes, activated peripheral blood monocytes, and neutrophils.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising a nucleotide sequence of SEQ ID NO: 1 or SEQ ID NO: 3; and
   b) a nucleic acid molecule consisting of nucleotides of SEQ ID NO: 1 or 3 encoding the MCT domain of 25466 (amino acids 40 to 477 of SEQ ID NO: 2).

2. The isolated nucleic acid molecule of claim 1, which is selected from the group consisting of
   a nucleic acid molecule comprising the nucleotide sequence of SEQ ID NO: 1 or SEQ ID NO: 3.

3. The nucleic acid molecule of claim 1 further comprising vector nucleic acid sequences.

4. The nucleic acid molecule of claim 1 further comprising nucleic acid sequences encoding a heterologous polypeptide.

5. A purified non-human host cell which contains the nucleic acid molecule of claim 1.

6. A purified non-human mammalian host cell containing the nucleic acid molecule of claim 1.

7. A non-human mammalian host cell containing the nucleic acid molecule of claim 1.

8. A method for producing a polypeptide selected from the group consisting of:
   a) a polypeptide comprising the amino acid sequence of SEQ ID NO: 2;
   b) a polypeptide consisting of the MCT domain (amino acids 40 to 477 of SEQ ID NO: 2) of 25466, wherein the MCT domain binds a monocarboxylated ion;

comprising culturing the host cell of claim 5 under conditions in which the nucleic acid molecule is expressed.

9. A purified non-human host cell which expressed the nucleic acid molecule of claim 1.

10. The host cell of claim 9 which is a mammalian host cell.

11. An isolated nucleic acid molecule, consisting of a nucleic acid sequence selected from the group consisting of:
   a) SEQ ID NO: 1; and
   b) SEQ ID NO: 3

* * * * *